(12) United States Patent
Nicolette

(10) Patent No.: US 8,029,796 B2
(45) Date of Patent: Oct. 4, 2011

(54) THERAPEUTIC ANTI-CYTOMEGALOVIRUS COMPOUNDS

(75) Inventor: Charles A. Nicolette, Framingham, MA (US)

(73) Assignee: Genzyme Corporation, Cambridge, MA (US)

( * ) Notice: Subject to any disclaimer, the term of this patent is extended or adjusted under 35 U.S.C. 154(b) by 1080 days.

(21) Appl. No.: 11/707,321

(22) Filed: Feb. 16, 2007

(65) Prior Publication Data

US 2009/0148451 A1 Jun. 11, 2009

Related U.S. Application Data

(60) Division of application No. 10/434,982, filed on May 10, 2003, now Pat. No. 7,202,331, which is a continuation of application No. 09/812,079, filed on Mar. 19, 2001, now Pat. No. 6,579,970.

(60) Provisional application No. 60/191,050, filed on Mar. 21, 2000, provisional application No. 60/254,989, filed on Dec. 12, 2000.

(51) Int. Cl.
A61K 39/245 (2006.01)
A61K 38/08 (2006.01)
C07K 7/06 (2006.01)

(52) U.S. Cl. .................. 424/185.1; 424/230.1; 530/328; 514/21.6

(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 5,440,013 A | 8/1995 | Kahn |
| 5,837,249 A | 11/1998 | Heber-Katz et al. |

FOREIGN PATENT DOCUMENTS

| | | |
|---|---|---|
| EP | 0702 082 A1 | 3/1996 |
| FR | 2 757 169 | 6/1998 |
| WO | WO 96/23060 | 8/1996 |
| WO | WO98/21233 A2 | 5/1998 |
| WO | WO 99/02183 | 1/1999 |
| WO | WO 99/36568 A | 7/1999 |

OTHER PUBLICATIONS

Parker et al (Journal of Immunology 149:3580-3587, 1992).*
Slansky et al (Immunity 13:529-538, 2000).*
Gavin et al (European Journal of Immunology 24:2124-2133, 1994).*
Altman, J.D. et al., "Phenotypic analysis of antigen-specific T lymphocytes" (1996) *Science* 274(5284):94-96.
Bertoni, R. et al., "Human class I supertypes and CTL repertoires extend to chimpanzees" (1998) *J. Immunol.* 161:4447-55.
Boczkowski, D. et al., "Dendritic cells pulsed with RNA are potent antigen-presenting cells in vitro and in vivo" (1996) *J. Exp. Med.* 184:465-72.
Bordignon, C. et al., "Retroviral vector-mediated high-efficiency expression of adenosine deaminase (ADA) in hematopoietic long-term cultures of ADA-deficient marrow cells" (1989) *Proc. Natl. Acad. Sci. USA* 86:6748-52.
Carter, B.J., "Adeno-associated virus vectors" (1992) *Curr. Op. Biotechnol.* 3:533-39.
Caruso, A. et al., "Flow cytometric analysis of activation markers on stimulated T cells and their correlation with cell proliferation" (1997) *Cytometry* 27:71-76.
Correll, P.H. et al., "Production of human glucocerebrosidase in mice after retroviral gene transfer into multipotential hematopoietic progenitor cells" (1989) *Proc. Natl. Acad. Sci. USA* 86:8912-16.
Coulie, P.G., "Human tumor antigens recognized by T cells: new perspectives for anti-cancer vaccines?" (1997) *Molec. Med. Today* 3:261-68.
Culver, K., et al., "Lymphocytes as cellular vehicles for gene therapy in mouse and man" (1991) *Proc. Natl. Acad. Sci. USA* 88:3155-59.
Dharanipragada, R. et al., "The absolute configuration of an intermediate in the asymmetric synthesis of unusual amino acids" (1992) *Acta. Cryst.* C48:1239-41.
Dharanipragada, R. et al., "Synthetic linear and cyclic glucagon antagonists" (1993) *Int. J. Peptide Protein Res.* 42(1):68-77.
DiMaio, J. et al., "Synthesis of chiral piperazin-2-ones as model peptidomimetics" (1989) *J. Chem. Soc. Perkin Trans.* 1(9):1687-89.
Feltkamp, M.C.W. et al., "Competition inhibition of cytotoxic T-lymphocyte (CTL) lysis, a more sensitive method to identify candidate CTL epitopes than induction of antibody-detected MHC class I stabilization" (1995) *Immunol. Lett.* 47:1-8.
Ferguson, et al. "Cell-surface anchoring of proteins via glycosylphosphatidylinositol structures" (1988) *Ann. Rev. Biochem.* 57:285-320.
Fujihashi, K. et al., "Cytokine-specific ELISPOT assay single cell analysis of IL-2, IL-4 and IL-6 producing cells" (1993) *J. Immunol. Meth.* 160:181-89.
Garvey D.S. et al., "3,4-disubstituted γ-lactam rings as conformationally constrained mimics of peptide derivatives containing aspartic acid or norleucine" (1990) *J. Org. Chem.* 55(3):936-40.
Hruby, V.J., "Conformational restrictions of biologically active peptides via amino acid side chain groups" (1982) *Life Sciences* 31:189-99.
Hruby, V.J. et al., "Emerging approaches in the molecular design of receptor-selective peptide ligands: conformational, topographical and dynamic considerations" (1990) *Biochem. J.* 268:249-62.
Isakov, N. et al., "ZAP-70 binding specificity to T cell receptor tyrosine-based activation motifs: The tandem SH2 domains of ZAP-70 bind distinct tyrosine-based activation motifs with varying affinity" (1995) *J. Exp. Med.* 181:375-80.
Jones, R.C.F. and G. J. Ward, "Amide bond isosteres: imidazolines in pseudopeptide chemistry" (1988) *Tetrahedron Lett.*, 29(31)3853-56.

(Continued)

*Primary Examiner* — Mary E Mosher

(74) *Attorney, Agent, or Firm* — Paul G. Alloway; B. Timothy Creagan

(57) ABSTRACT

The present invention provides synthetic compounds, antibodies that recognize and bind to these compounds, polynucleotides that encode these compounds, and immune effector cells raised in response to presentation of these epitopes. The invention further provides methods for inducing an immune response and administering immunotherapy to a subject by delivering the compositions of the invention.

2 Claims, No Drawings

OTHER PUBLICATIONS

Kahn, M. and S. Bertenshaw, "The incorporation of β-turn prosthetic units into Merrifield solid phase peptide synthesis" (1989) *Tetrahedron Lett.* 30(18):2317-20.

Karlsson, S. et al., "Stable gene transfer and tissue-specific expression of a human globin gene using adenoviral vectors" (1986) *EMBO J.* 5(9):2377-85.

Kawakami, Y. et al., "Cloning of the gene coding for a shared human melanoma antigen recognized by autologous T cells infiltrating into tumor" (1994) *Proc. Natl Acad. Sci. USA* 91(9):3515-19.

Kazmierski, W.M. and V. J. Hruby, "Asymmetric synthesis of topographically constrained amino acids: synthesis of the optically pure isomers of α,β-dimethyl-phenylalanine and α,β-dimethyl-1,2,3,4-tetrahydroisoquinoline-3-carboxylic acid" (1991) *Tetrahedron Lett.* 32(41):5769-72.

Kazmierski, W.M. et al., "Topographic design of peptide neurotransmitters and hormones on stable backbone templates: relation of conformation and dynamics to bioactivity" (1991) *J. Am. Chem. Soc.* 113:2275-83.

Kemp, D.S. and P.E. McNamara, "Conformationally restricted cyclic nonapeptides derived from L-cysteine and LL-3-amino-2-piperidone-6-carboxylic acid (LL-Acp), A potent β-turn-inducing dipeptide analogue" (1985) *J. Org. Chem.* 50:5834-38.

Kemp, D.S. and B.R. Bowen, "Conformational analysis of peptide-functionalized diacylaminoepindolidiones $^1$H NMR evidence for β-sheet formation" (1988) *Tetrahedron Lett.* 29(40):5081-82.

Kemp, D.S. and W.E. Stites, "A convenient preparation of derivatives of 3(S)-amino-10(R)-carboxy-1,6-diaza-cyclodeca-2,7-dione; The dilactam of L-α,γ-diaminobutyric acid and D-glutamic acid: A β-turn template" (1988) *Tetrahedron Lett.* 29(40):5057-60.

Kemp, D.S. and T.P. Curran, "(2,5S, 8S, 11S)-1-acetyl-1,4-diaza-3-keto-5-carboxy-10-thia-tricyclo-[2.8.0$^{4,8}$]-ridecane, 1 the preferred conformation of 1 (1=αtemp-OH) and its peptide conjugates αtemp-L-(Ala)$_a$-OR(n=1 to 4) and α-temp-L-Ala-L-Phe-Lys(ε-Boc)-NHMe studies of templates for α-helix formation" (1988) *Tetrahedron Lett.* 29(39):4935-38.

Kemp, D.S. and J.S. Carter, "Amino acid derivatives that stabilize secondary structures of polypeptides. 4. Practical synthesis of 4-(alkylamino)-3-cyano-6-azabicyclo[3.2.1]oct-3-enes (ben derivatives) as γ-turn templates" (1989) *J. Org. Chem.* 54:109-115.

McLaughlin-Taylor, et al., "Identification of the Major Late Human Cytomegalovirus Matrix Protein pp65 as a Target Antigen for CD8+ Virus-Specific Cytotoxic T Lymphocytes" (1994) *J. Medical Virology*, 43:103-110.

McGrory, W.J. et al., "Short communications: A simple technique for the rescue of early region 1 mutation into infectious human adenovirus type 5" (1988) *Virology* 163:614-17.

Merrifield, R.B., "New approaches to the chemical synthesis of peptides" (1967) *Recent Progress in Hormone Res.* 23:451-482.

Miyake, A. et al., "Synthesis and angiotensin converting enzyme inhibitory activity of 1,2,3,4-tetrahydroisoquinoline-3-carboxylic acid derivatives" (1984) *J. Takeda Res. Labs.* 43(3/4):53-76.

Mosier, D.E. et al., "Resistance to human immunodeficiency virus 1 infection of SCID mice reconstituted with peripheral blood leukocytes from donors vaccinated with vaccinia gp160 and recombinant gp160" (1993) *Proc. Natl. Acad. Sci. USA* 90:2443-47.

Muzcyzka, "Use of adeno-associated virus as a general transduction vector for mammalian cells" (1992) *Curr. Top. Microbiol. Immunol.* 158:97-129.

Nagai, U. and K. Sato, "Synthesis of a bicyclic dipeptide with the shape of β-turn central part" (1985) *Tetrahedron Lett.* 26(5):647-50.

Nair, S. et al., "Soluble proteins delivered to dendritic cells via pH-sensitive liposomes induce primary cytotoxic T lymphocyte responses in vitro" (1992) *J. Exp. Med.* 175:609-612.

Olson, G.L. et al., "Design and synthesis of a protein β-turn mimetic" (1990) *J. Am. Chem. Soc.* 112:323-33.

Paglia, P. et al., "Murine dendritic cells loaded in vitro with soluble protein prime cytotoxic T lymphocytes against tumor antigen in vivo" (1996) *J. Exp. Med.* 183:317-22.

Pardoll, D.M., "Cancer vaccines" (1998) *Nature Med.* 4(5 Suppl.):525-531.

Parker, et al., "Sequence motifs important for peptide binding to the human MHC class 1 molecule, HLA-A2" (1992) *J. Immunol.* 149(11):3580-87.

Parkhurst, M.R. et al., "Improved induction of melanoma-reactive CTL with peptides from the melanoma antigen gp100 modified at HLA-A *0201-binding residues" (1996) *J. Immunol.* 157:2539-48.

al-Ramadi, B.K. et al., "Lack of strict correlation of functional sensitization with the apparent affinity of MHC/peptide complexes for the TCR" (1992) *J. Immunol.* 155(2):662-673.

Rill, D.R. et al., "An approach for the analysis of relapse and marrow reconstitution after autologous marrow transplantation using retrovirus-mediated gene transfer" (1992) *Blood* 79(10):2694-700.

Rouse, R.J.D. et al., "Induction in vitro of primary cytotoxic T-lymphocyte responses with DNA encoding herpes simplex virus proteins" (1994) *J. Virol.* 68(9):5685-89.

Salazar, E. et al., "Agonist peptide from a cytotoxic T-lymphocyte epitope of human carcinoembryonic antigen stimulates production of TC1-type cytokines and increases tyrosine phosphorylation more efficiently than cognate peptide" (2000) *Int. J. Cancer* 85:829-838.

Samanen, J. et al., "5,5-dimethylthiazolidine-4-carboxylic acid (DTC) as a proline analog with restricted conformation" (1990) *Int. J. Peptide Protein Res.* 35:501-509.

Schlesinger, S. and T.W. Dubensky, Jr., "Alphavirus vectors for gene expression and vaccines" (1999) *Curr Opin Biotechnol.* 10(5):434-439.

Sette, A. et al., "The relationship between class 1 binding affinity and immunogenicity of potential cytotoxic T cell epitopes" (1994) *J. Immunol.* 153(12):5586-92.

Shirai, M. et al., "CTL responses of HLA-A2.1-transgenic mice specific for hepatitis C viral peptides predict epitopes for CTL of humans carrying HLA-A2.1" (1995) *J. Immunol.* 154:2733-42.

Stuber, G. et al., "HLA-A0201 and HLA-B7 binding peptides in the EBV-encoded EBNA-1, EBNA-2 and BZLF-1 proteins detected in the MHC class 1 stabilization assay. Low proportion of binding motifs for several HLA class 1 alleles in EBNA-1" (1995) *Int. Immunol.* 7(4):653-663.

Tan, L. et al., "An improved assembly assay for peptide binding to HLA-B*2705 and H-2K*class 1 MHC molecules" (1997) *J. Immunol. Meth.* 209(1):25-36.

Tanguay, S. and J.J. Killon, "Direct comparison of ELISPOT and ELISA-based asssays for detection of individual cytokine-secreting cells" (1994) *Lymphokine Cytokine Res.* 13(4):259-263.

Valmoni, D. et al., "Induction of potent antitumor CTL responses by recombinant vaccinia encoding a melan-A peptide analogue" (2000) *J. Immunol.* 164(2):1125-31.

van der Burg, S.H. et al., "Immunogenicity of peptides bound to MHC class 1 molecules depends on the MHC-peptide complex stability" (1996) *J. Immunol.* 156:3308-14.

Ware, C.F. et al., "Recognition of HLA-A2 mutant and variant target cells by an HLA-A2 allospecific human cytotoxic T lymphocyte line" (1983) *J. Immunol.* 131(3):1312-17.

Wilchek, M. and E.A. Bayer, "The avidin-biotin complex in bioanalytical applications" (1988) *Anal. Biochem.* 171:1-32.

Ying, H. et al., "Cancer therapy using a self-replicating RNA vaccine" (1999) *Nat. Med.* 5(7):823-827.

Zabrocki, J. et al., "Conformational mimicry, 1. 1,5-disubstituted tetrazole ring as a surrogate for the cis amide bond" (1988) *J. Am. Chem. Sci.* 110:5875-80.

Zechel, C. et al., "Synthetic glucagon antagonists and partial agonists" (1991) *Int. J. Pep. Protein Res.* 38(2):131-138.

Zuegel, et al., "Termination of peripheral tolerance to a T cell epitope by heteroclitic antigen analogues" (1998) *J. Immunol.* 161(4):1705-09.

Zweerink, H.J. et al., "Presentation of endogenous peptides to MHC class 1-restricted cytotoxic T lymphocytes in transport deletion mutant T2 cells" (1993) *J. Immunol.* 150(5):1763-71.

Colona, M. et al., "Cloning of Immunoglobulin-Superfamily Members Associated with HLA-C and HLA-B Recognition by Human Natural Killer Cells" (1995) *Science*, 268:405-408.

Cockle, S.M. et al., "Thyrotrophin-releasing hormone-related polypeptides in rabbit prostate and semen are different from those in rabbit hypothalamus" (1989) *J. Endocrinology*, 120:31-36.

Rotzschke, O. and K. Falk, "Naturally-occurring peptide antigens derived from the MHC class-1-restricted processing pathway" (1991) *Immunology Today*, 12(12):447-55.

Miltenyi Biotec's CMV pp65-recombinant protein human cytomegalovirus.

Chen, J.-L. et al., "Identification of NY-ESO-1 Peptide Analogues Capable of Improved Stimulation of Tumor-Reactive CTL", (2000) *J. Immunol. 165*:948-55.

\* cited by examiner

THERAPEUTIC ANTI-CYTOMEGALOVIRUS COMPOUNDS

CROSS-REFERENCE TO RELATED APPLICATIONS

This application is a divisional application of U.S. application Ser. No. 10/434,982 filed May 10, 2003 now U.S. Pat. No. 7,202,331 which is a continuation application of U.S. application Ser. No. 09/812,079 filed Mar. 19, 2001, now U.S. Pat. No. 6,579,970, which claims priority under 35 U.S.C. §119(e) to U.S. Provisional Patent Application Ser. Nos. 60/191,050 and 60/254,989, filed Mar. 21, 2000 and Dec. 12, 2000, respectively. The entire contents of these applications are hereby incorporated by reference into the present disclosure.

TECHNICAL FIELD

The invention relates to the field of therapeutic compounds useful against Cytomegalovirus ("CMV") infections.

BACKGROUND OF THE INVENTION

The recognition of antigenic epitopes presented by molecules of the Major Histocompatibility Complex (MHC) plays a central role in the establishment, maintenance and execution of mammalian immune responses. T cell surveillance and recognition of peptide antigens presented by cell surface MHC molecules expressed by somatic cells and antigen presenting leukocytes functions to control invasion by infectious organisms such as viruses, bacteria, and parasites. In addition it has now been demonstrated that antigen-specific cytotoxic T lymphocytes (CTLs) can recognize certain cancer cell antigens and attack cells expressing these antigens. This T cell activity provides a basis for developing novel strategies for anti-cancer vaccines. Furthermore, inappropriate T cell activation plays a central role in certain debilitating autoimmune diseases such as rheumatoid arthritis, multiple sclerosis, and asthma. Thus presentation and recognition of antigenic epitopes presented by MHC molecules play a central role in mediating immune responses in multiple pathological conditions.

Tumor specific T cells, derived from cancer patients, will bind and lyse tumor cells. This specificity is based on their ability to recognize short amino acid sequences (epitopes) presented on the surface of the tumor cells by MHC class I and, in some cell types, class II molecules. These epitopes are derived from the proteolytic degradation of intracellular proteins called tumor antigens encoded by genes that are either uniquely or aberrantly expressed in tumor or cancer cells.

The availability of specific anti-tumor T cells has enabled the identification of tumor antigens and subsequently the generation of cancer vaccines designed to provoke an anti-tumor immune response. Anti-tumor T cells are localized within cancer patients, including in the blood (where they can be found in the peripheral blood mononuclear cell fraction), in primary and secondary lymphoid tissue, e.g., the spleen, in ascites fluid in ovarian cancer patients (tumor associated lymphocytes or TALs) or within the tumor itself (tumor infiltrating lymphocytes or TILs). Of these, TILs have been the most useful in the identification of tumor antigens and tumor antigen-derived peptides recognized by T cells.

Conventional methods to generate TILs involve mincing tumor biopsy tissue and culturing the cell suspension in vitro in the presence of the T cell growth factor interleukin 2 (IL-2). Over a period of several days, the combination of the tumor cells and IL-2 can stimulate the proliferation of tumor specific T cells at the expense of tumor cells. In this way, the T cell population is expanded. The T cells derived from the first expansion are subsequently mixed with either mitomycin C-treated or irradiated tumor cells and cultured in vitro with IL-2 to promote further proliferation and enrichment of tumor reactive T cells. After several rounds of in vitro expansion, a potent anti-tumor T cell population can be recovered and used to identify tumor antigens via conventional but tedious expression cloning methodology. Kawakami Y. et al. (1994) Proc. Natl. Acad. Sci. USA 91(9):3515-3519.

This currently employed methodology used to generate tumor specific T cells in vitro is unreliable and the antigens identified by this method do not necessarily induce an anti-tumor immune response. Numerous experiments demonstrate that the encounter of antigens by mature T cells often results in the induction of tolerance because of ignorance, anergy or physical deletion. Pardoll (1998) Nature Med. 4(5): 525-531.

The ability of a particular peptide to function as a T cell epitope requires that it bind effectively to the antigen presenting domain of an MHC molecule and also that it display an appropriate set of amino acids that can be specifically recognized by a T cell receptor molecule. While it is possible to identify natural T cell epitopes derived from antigenic polypeptides, these peptide epitopes do not necessarily represent antigens that are optimized for inducing a particular immune response. In fact, it has been shown that it is possible to improve the effectiveness of natural epitopes by introducing single amino or multiple acids substitutions that alter their sequence (Valmori et al. (2000) J. Immunol. 164(2):1125-1131). Thus, delivery of carefully optimized synthetic peptide epitopes has the potential to provide an improved method to induce a useful immune response.

The introduction into an animal of an antigen has been widely used for the purposes of modulating the immune response, or lack thereof, to the antigen for a variety of purposes. These include vaccination against pathogens, induction of an immune response to a cancerous cell, reduction of an allergic response, reduction of an immune response to a self antigen that occurs as a result of an autoimmune disorder, reduction of allograft rejection, and induction of an immune response to a self antigen for the purpose of contraception.

In the treatment of cancer, a variety of immunotherapeutic approaches have been taken to generate populations of cytotoxic T lymphocytes which specifically recognize and lyse tumor cells. Many of these approaches depend in part on identifying and characterizing tumor-specific antigens.

More recently, certain pathogen- and tumor-related proteins have been immunologically mimicked with synthetic peptides whose amino acid sequence corresponds to that of an antigenic determinant domain of the pathogen- or tumor-related protein. Despite these advances, peptide immunogens based on native sequences generally perform less than optimally with respect to inducing an immune response. Thus, a need exists for modified synthetic antigenic peptide epitopes with enhanced immunomodulatory properties. This invention satisfies this need and provides related advantages as well.

DISCLOSURE OF THE INVENTION

The present invention provides novel synthetic therapeutic compounds. These compounds are designed to enhance binding to MHC molecules and to enhance immunoregulatory properties relative to their natural counterparts. The synthetic compounds of the invention are useful to modulate an immune response to the synthetic and naturally occurring compounds.

Further provided are polynucleotides encoding the compounds of the invention, gene delivery vehicles comprising these polynucleotides and host cells comprising these polynucleotides.

In addition, the invention provides methods for inducing an immune response in a subject by delivering the compounds and compositions of the invention, and delivering these in the context of an MHC molecule.

The compounds of the invention are also useful to generate antibodies that specifically recognize and bind to these molecules. These antibodies are further useful for immunotherapy when administered to a subject.

The invention also provides immune effector cells raised in vivo or in vitro in the presence and at the expense of an antigen presenting cell that presents the peptide compositions of the invention in the context of an MHC molecule and a method of adoptive immunotherapy comprising administering an effective amount of these immune effector cells to a subject.

DESCRIPTION OF THE SEQUENCE LISTING

SEQ ID NO:1. The complete nucleotide sequence of a cDNA encoding the CMV antigen pp65.

SEQ ID NO:2. The amino acid sequence of the native CMV antigen pp65. The compounds of the invention are variations based on native pp65 peptide 495-503.

SEQ ID NO:3. The amino acid sequence of compound 1.
SEQ ID NO:4. The polynucleotide sequence encoding compound 1.
SEQ ID NO:5. The amino acid sequence of compound 2.
SEQ ID NO:6. The polynucleotide sequence encoding compound 2.
SEQ ID NO:7. The amino acid sequence of compound 3.
SEQ ID NO:8. The polynucleotide sequence encoding compound 3.
SEQ ID NO:9. The amino acid sequence of compound 4.
SEQ ID NO:10. The polynucleotide sequence encoding compound 4.
SEQ ID NO:11. The amino acid sequence of compound 5.
SEQ ID NO:12. The polynucleotide sequence encoding compound 5.
SEQ ID NO:13. The amino acid sequence of compound 6.
SEQ ID NO:14. The polynucleotide sequence encoding compound 6.
SEQ ID NO:15. The amino acid sequence of the native pp65 antigenic peptide 495-503.

MODES OF CARRYING OUT THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. These methods are described in the following publications. See, e.g., Sambrook et al. MOLECULAR CLONING: A LABORATORY MANUAL, 2$^{nd}$ edition (1989); CURRENT PROTOCOLS IN MOLECULAR BIOLOGY (F. M. Ausubel et al. eds. (1987)); the series METHODS IN ENZYMOLOGY (Academic Press, Inc.); PCR: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1988)); and ANIMAL CELL CULTURE (R. I. Freshney ed. (1987)).

DEFINITIONS

As used herein, certain terms may have the following defined meanings.

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The term "antigen" is well understood in the art and includes substances which are immunogenic, i.e., immunogens, as well as substances which induce immunological unresponsiveness, or anergy, i.e., anergens.

An "altered antigen" is one having a primary sequence that is different from that of the corresponding wild-type antigen. Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand. (Ferguson et al. (1988) Ann. Rev. Biochem. 57:285-320). A synthetic or altered antigen of the invention is intended to bind to the same TCR as the natural epitope.

A "self-antigen" also referred to herein as a native or wild-type antigen is an antigenic peptide that induces little or no immune response in the subject due to self-tolerance to the antigen. An example of a self-antigen is the melanoma specific antigen gp100.

The term "tumor associated antigen" or "TAA" refers to an antigen that is associated with or specific to a tumor. Examples of known TAAs include gp100, MART and MAGE.

The terms "major histocompatibility complex" or "MHC" refers to a complex of genes encoding cell-surface molecules that are required for antigen presentation to T cells and for rapid graft rejection. In humans, the MHC is also known as the "human leukocyte antigen" or "HLA" complex. The proteins encoded by the MHC are known as "MHC molecules" and are classified into class I and class II MHC molecules. Class I MHC includes membrane heterodimeric proteins made up of an α chain encoded in the MHC noncovalently linked with the β2-microglobulin. Class I MHC molecules are expressed by nearly all nucleated cells and have been shown to function in antigen presentation to $CD8^+$ T cells. Class I molecules include HLA-A, B, and C in humans. Class II MHC molecules also include membrane heterodimeric proteins consisting of noncovalently associated α and β chains. Class II MHC molecules are known to function in $CD4^+$ T cells and, in humans, include HLA-DP, -DQ, and DR. In a preferred embodiment, invention compositions and ligands can complex with MHC molecules of any HLA type. Those of skill in the art are familiar with the serotypes and genotypes of the HLA. See: http://bimas.dcrt.nih.gov/cgi-bin/molbio/hla_coefficient_viewing_page. Rammensee H. G., Bachmann J., and Stevanovic S. MHC Ligands and Peptide Motifs (1997) Chapman & Hall Publishers; Schreuder G. M. Th. et al. The HLA dictionary (1999) Tissue Antigens 54:409-437.

The term "antigen-presenting matrix", as used herein, intends a molecule or molecules which can present antigen in such a way that the antigen can be bound by a T-cell antigen receptor on the surface of a T cell. An antigen-presenting matrix can be on the surface of an antigen-presenting cell (APC), on a vesicle preparation of an APC, or can be in the form of a synthetic matrix on a solid support such as a bead or a plate. An example of a synthetic antigen-presenting matrix is purified MHC class I molecules complexed to β2-microglobulin, multimers of such purified MHC class I molecules, purified MHC Class II molecules, or functional portions thereof, attached to a solid support.

The term "antigen presenting cells (APC)" refers to a class of cells capable of presenting one or more antigens in the form of antigen-MHC complex recognizable by specific effector cells of the immune system, and thereby inducing an effective cellular immune response against the antigen or antigens being presented. While many types of cells may be capable of presenting antigens on their cell surface for T-cell recognition, only professional APCs have the capacity to present antigens in an efficient amount and further to activate T-cells for cytotoxic T-lymphocyte (CTL) responses. APCs can be intact whole cells such as macrophages, B-cells and dendritic cells; or other molecules, naturally occurring or synthetic, such as purified MHC class I molecules complexed to β2-microglobulin.

The term "dendritic cells (DC)" refers to a diverse population of morphologically similar cell types found in a variety of lymphoid and non-lymphoid tissues (Steinman (1991) Ann. Rev. Immunol. 9:271-296). Dendritic cells constitute the most potent and preferred APCs in the organism. A subset, if not all, of dendritic cells are derived from bone marrow progenitor cells, circulate in small numbers in the peripheral blood and appear either as immature Langerhans' cells or terminally differentiated mature cells. While the dendritic cells can be differentiated from monocytes, they possess distinct phenotypes. For example, a particular differentiating marker, CD14 antigen, is not found in dendritic cells but is possessed by monocytes. Also, mature dendritic cells are not phagocytic, whereas the monocytes are strongly phagocytosing cells. It has been shown that DCs provide all the signals necessary for T cell activation and proliferation.

The term "antigen presenting cell recruitment factors" or "APC recruitment factors" include both intact, whole cells as well as other molecules that are capable of recruiting antigen presenting cells. Examples of suitable APC recruitment factors include molecules such as interleukin 4 (IL4), granulocyte macrophage colony stimulating factor (GM-CSF), Sepragel and macrophage inflammatory protein 3 alpha (MIP3α). These are available from Immunex, Schering-Plough and R&D Systems (Minneapolis, Minn.). They also can be recombinantly produced using the methods disclosed in CURRENT PROTOCOLS IN MOLECULAR BIOLOGY (F. M. Ausubel et al., eds. (1987)). Peptides, proteins and compounds having the same biological activity as the above-noted factors are included within the scope of this invention.

The term "immune effector cells" refers to cells capable of binding an antigen and which mediate an immune response. These cells include, but are not limited to, T cells, B cells, monocytes, macrophages, NK cells and cytotoxic T lymphocytes (CTLs), for example CTL lines, CTL clones, and CTLs from tumor, inflammatory, or other infiltrates. Certain diseased tissue expresses specific antigens and CTLs specific for these antigens have been identified. For example, approximately 80% of melanomas express the antigen known as gp100.

The term "immune effector molecule" as used herein, refers to molecules capable of antigen-specific binding, and includes antibodies, T cell antigen receptors, and MHC Class I and Class II molecules.

A "naïve" immune effector cell is an immune effector cell that has never been exposed to an antigen capable of activating that cell. Activation of naïve immune effector cells requires both recognition of the peptide:MHC complex and the simultaneous delivery of a costimulatory signal by a professional APC in order to proliferate and differentiate into antigen-specific armed effector T cells.

"Immune response" broadly refers to the antigen-specific responses of lymphocytes to foreign substances. Any substance that can elicit an immune response is said to be "immunogenic" and is referred to as an "immunogen". All immunogens are antigens, however, not all antigens are immunogenic. An immune response of this invention can be humoral (via antibody activity) or cell-mediated (via T cell activation).

The term "ligand" as used herein refers to any molecule that binds to a specific site on another molecule. In other words, the ligand confers the specificity of the protein in a reaction with an immune effector cell. It is the ligand site within the protein that combines directly with the complementary binding site on the immune effector cell.

In a preferred embodiment, a ligand of the invention binds to an antigenic determinant or epitope on an immune effector cell, such as an antibody or a T cell receptor (TCR). A ligand may be an antigen, peptide, protein or epitope of the invention.

Invention ligands may bind to a receptor on an antibody. In one embodiment, the ligand of the invention is about 4 to about 8 amino acids in length.

Invention ligands may bind to a receptor on an MHC class I molecule. In one embodiment, the ligand of the invention is about 7 to about 11 amino acids in length.

Invention ligands may bind to a receptor on an MHC class II molecule. In one embodiment, the ligand of the invention is about 10 to about 20 amino acids long.

As used herein, the term "educated, antigen-specific immune effector cell", is an immune effector cell as defined above, which has previously encountered an antigen. In contrast with its naïve counterpart, activation of an educated, antigen-specific immune effector cell does not require a costimulatory signal. Recognition of the peptide:MHC complex is sufficient.

"Activated", when used in reference to a T cell, implies that the cell is no longer in $G_0$ phase, and begins to produce one or more of cytotoxins, cytokines, and other related membrane-associated proteins characteristic of the cell type (e.g., $CD8^+$ or $CD4^+$), is capable of recognizing and binding any target cell that displays the particular antigen on its surface, and releasing its effector molecules.

In the context of the present invention, the term "recognized" intends that a composition of the invention, comprising one or more ligands, is recognized and bound by an immune effector cell wherein such binding initiates an effective immune response. Assays for determining whether a ligand is recognized by an immune effector cell are known in the art and are described herein.

The term "preferentially recognized" intends that the specificity of a composition or ligand of the invention is restricted to immune effector cells that recognize and bind the native ligand.

The term "cross-reactive" is used to describe compounds of the invention which are functionally overlapping. More particularly, the immunogenic properties of a native ligand and/or immune effector cells activated thereby are shared to a certain extent by the altered ligand such that the altered ligand is "cross-reactive" with the native ligand and/or the immune effector cells activated thereby. For purposes of this invention, cross-reactivity is manifested at multiple levels: (i) at the ligand level, e.g., the altered ligands can bind the TCR of and activate native ligand CTLs; (ii) at the T cell level, i.e., altered ligands of the invention bind the TCR of and activate a population of T cells (distinct from the population of native ligand CTLs) which can effectively target and lyse cells displaying the native ligand; and (iii) at the antibody level, e.g., "anti"-altered ligand antibodies can detect, recognize and bind the native ligand and initiate effector mechanisms in an immune response which ultimately result in elimination of the native ligand from the host.

As used herein, the term "inducing an immune response in a subject" is a term well understood in the art and intends that an increase of at least about 2-fold, more preferably at least about 5-fold, more preferably at least about 10-fold, more preferably at least about 100-fold, even more preferably at least about 500-fold, even more preferably at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

"Co-stimulatory molecules" are involved in the interaction between receptor-ligand pairs expressed on the surface of antigen presenting cells and T cells. Research accumulated over the past several years has demonstrated convincingly that resting T cells require at least two signals for induction of cytokine gene expression and proliferation (Schwartz R. H. (1990) Science 248:1349-1356 and Jenkins M. K. (1992) Immunol. Today 13:69-73). One signal, the one that confers specificity, can be produced by interaction of the TCR/CD3 complex with an appropriate MHC/peptide complex. The second signal is not antigen specific and is termed the "co-stimulatory" signal. This signal was originally defined as an activity provided by bone-marrow-derived accessory cells such as macrophages and dendritic cells, the so called "professional" APCs. Several molecules have been shown to enhance co-stimulatory activity. These are heat stable antigen (HSA) (Liu Y. et al. (1992) J. Exp. Med. 175:437-445), chondroitin sulfate-modified MHC invariant chain (Ii-CS) (Naujokas M. F. et al. (1993) Cell 74:257-268), intracellular adhesion molecule 1 (ICAM-1) (Van Seventer G. A. (1990) J. Immunol. 144:4579-4586), B7-1, and B7-2/B70 (Schwartz R. H. (1992) Cell 71:1065-1068). These molecules each appear to assist co-stimulation by interacting with their cognate ligands on the T cells. Co-stimulatory molecules mediate co-stimulatory signal(s), which are necessary, under normal physiological conditions, to achieve full activation of naïve T cells. One exemplary receptor-ligand pair is the B7 co-stimulatory molecule on the surface of APCs and its counter-receptor CD28 or CTLA-4 on T cells (Freeman et al. (1993) Science 262:909-911; Young et al. (1992) J. Clin. Invest. 90:229 and Nabavi et al. (1992) Nature 360:266-268). Other important co-stimulatory molecules are CD40, CD54, CD80, and CD86. The term "co-stimulatory molecule" encompasses any single molecule or combination of molecules which, when acting together with a peptide/MHC complex bound by a TCR on the surface of a T cell, provides a co-stimulatory effect which achieves activation of the T cell that binds the peptide. The term thus encompasses B7, or other co-stimulatory molecule(s) on an antigen-presenting matrix such as an APC, fragments thereof (alone, complexed with another molecule(s), or as part of a fusion protein) which, together with peptide/MHC complex, binds to a cognate ligand and results in activation of the T cell when the TCR on the surface of the T cell specifically binds the peptide. Co-stimulatory molecules are commercially available from a variety of sources, including, for example, Beckman Coulter, Inc. (Fullerton, Calif.). It is intended, although not always explicitly stated, that molecules having similar biological activity as wild-type or purified co-stimulatory molecules (e.g., recombinantly produced or muteins thereof) are intended to be used within the spirit and scope of the invention.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California).

The term "immunomodulatory agent", as used herein, is a molecule, a macromolecular complex, or a cell that modulates an immune response and encompasses a synthetic antigenic peptide of the invention alone or in any of a variety of formulations described herein; a polypeptide comprising a synthetic antigenic peptide of the invention; a polynucleotide encoding a peptide or polypeptide of the invention; a synthetic antigenic peptide of the invention bound to a Class I or a Class II MHC molecule on an antigen-presenting matrix, including an APC and a synthetic antigen-presenting matrix (in the presence or absence of co-stimulatory molecule(s)); a synthetic antigenic peptide of the invention covalently or non-covalently complexed to another molecule(s) or macromolecular structure; and an educated, antigen-specific immune effector cell which is specific for a peptide of the invention.

The term "modulate an immune response" includes inducing (increasing, eliciting) an immune response; and reducing (suppressing) an immune response. An immunomodulatory method (or protocol) is one that modulates an immune response in a subject.

As used herein, the term "cytokine" refers to any one of the numerous factors that exert a variety of effects on cells, for example, inducing growth or proliferation. Non-limiting examples of cytokines which may be used alone or in combination in the practice of the present invention include, interleukin 2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1I), interleukin II (IL-11), MIP-11, leukemia inhibitory factor (LIF), c-kit ligand, thrombopoietin (TPO) and flt3 ligand. The present invention also includes culture conditions in which one or more cytokine is specifically excluded from the medium. Cytokines are commercially available from several vendors such as, for example, Genzyme (Framingham, Mass.), Genentech (South San Francisco, Calif.), Amgen (Thousand Oaks, Calif.), R&D Systems (Minneapolis, Minn.) and Immunex (Seattle, Wash.). It is intended, although not always explicitly stated, that molecules having similar biological activity as wild-type or purified cytokines (e.g., recombinantly produced or muteins thereof) are intended to be used within the spirit and scope of the invention.

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules.

The term "peptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The term "genetically modified" means containing and/or expressing a foreign gene or nucleic acid sequence which in turn, modifies the genotype or phenotype of the cell or its progeny. In other words, it refers to any addition, deletion or disruption to a cell's endogenous nucleotides.

As used herein, "expression" refers to the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al. (1989) supra). Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" refers to a juxtaposition wherein the elements are in an arrangement allowing them to function.

A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr Opin Biotechnol. 10(5):434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., WO 95/27071. Ads are easy to grow and do not require integration into the host cell genome. Recombinant Ad-derived vectors, particularly those that reduce the potential for recombination and generation of wild-type virus, have also been constructed. See, WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., TCR, CD3 or CD4.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

The term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

"Host cell," "target cell" or "recipient cell" are intended to include any individual cell or cell culture which can be or have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, animal cells, and mammalian cells, e.g., murine, rat, simian or human.

A "subject" is a vertebrate, preferably a mammal, more preferably a human. Mammals include, but are not limited to, murines, simians, humans, farm animals, sport animals, and pets.

A "control" is an alternative subject or sample used in an experiment for comparison purpose. A control can be "positive" or "negative". For example, where the purpose of the experiment is to determine a correlation of an altered expression level of a gene with a particular type of cancer, it is generally preferable to use a positive control (a subject or a sample from a subject, carrying such alteration and exhibiting syndromes characteristic of that disease), and a negative control (a subject or a sample from a subject lacking the altered expression and clinical syndrome of that disease).

The terms "cancer," "neoplasm," and "tumor," used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

"Suppressing" tumor growth indicates a growth state that is curtailed compared to growth without contact with educated, antigen-specific immune effector cells described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and "suppressing" tumor growth indicates a growth state that is curtailed when stopping tumor growth, as well as tumor shrinkage.

The term "culturing" refers to the in vitro propagation of cells or organisms on or in media of various kinds. It is understood that the descendants of a cell grown in culture may not be completely identical (morphologically, genetically, or phenotypically) to the parent cell. By "expanded" is meant any proliferation or division of cells.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin REMINGTON'S PHARM. SCI., 15th Ed. (Mack Publ. Co., Easton (1975)).

An "effective amount" is an amount sufficient to effect beneficial or desired results. An effective amount can be administered in one or more administrations, applications or dosages.

The present invention provides compounds having the following structures:

(SEQ ID NO 3)

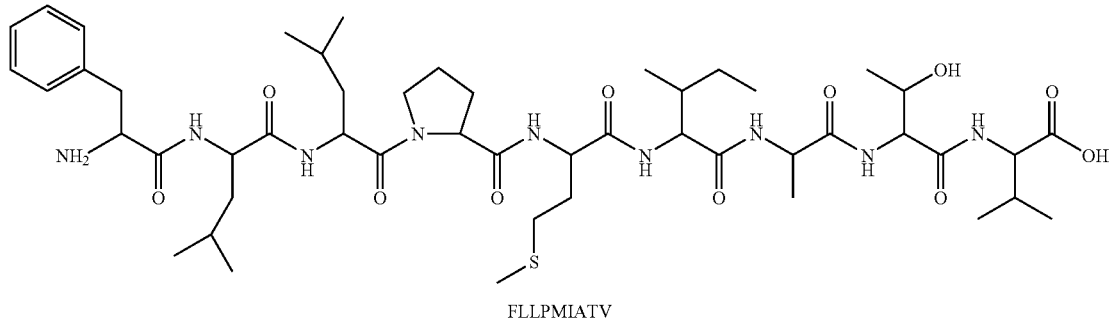

FLLPMIATV (SEQ ID NO 5)
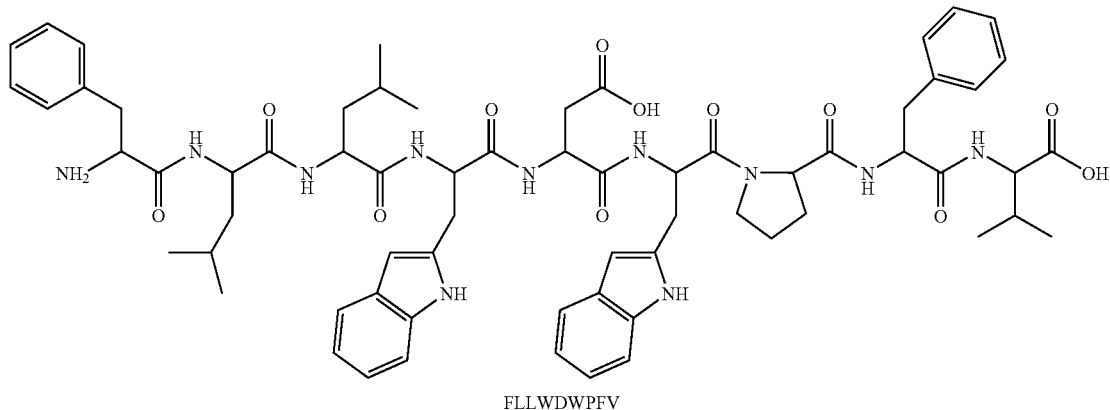
FLLWDWPFV
(SEQ ID NO 7)
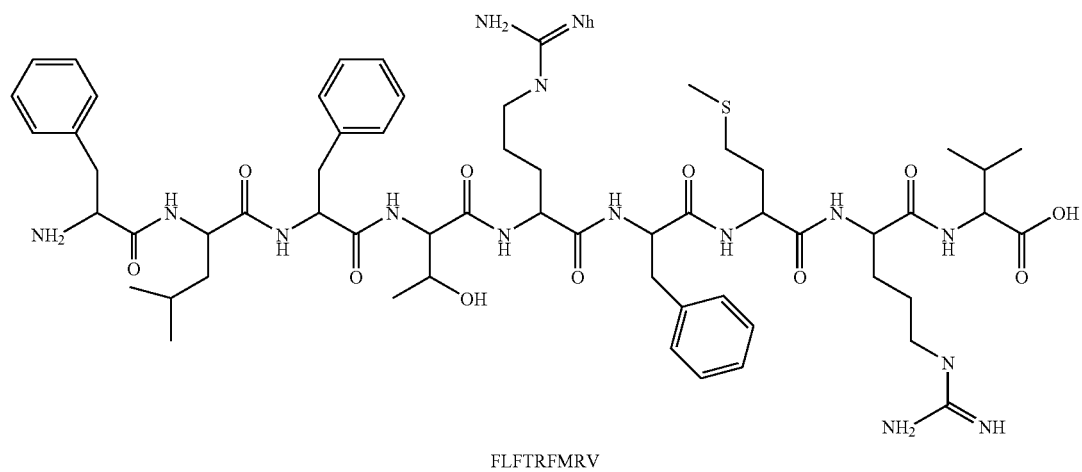
FLFTRFMRV
(SEQ ID NO 9)
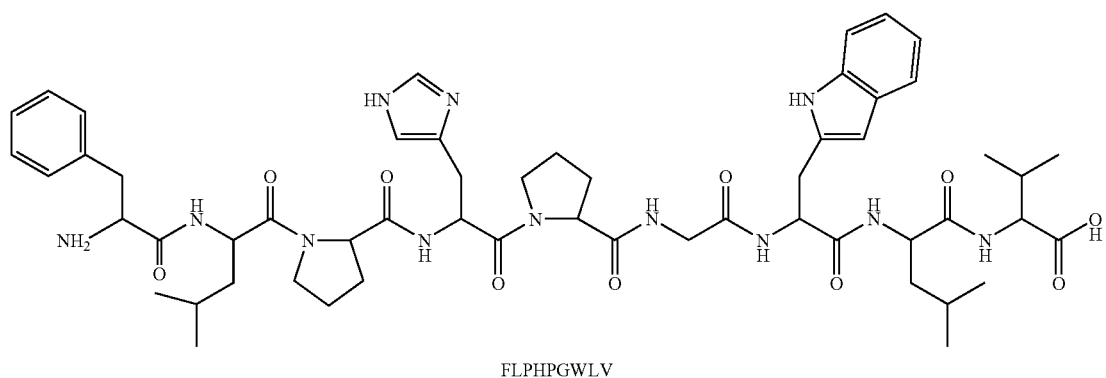
FLPHPGWLV (SEQ ID NO 11)

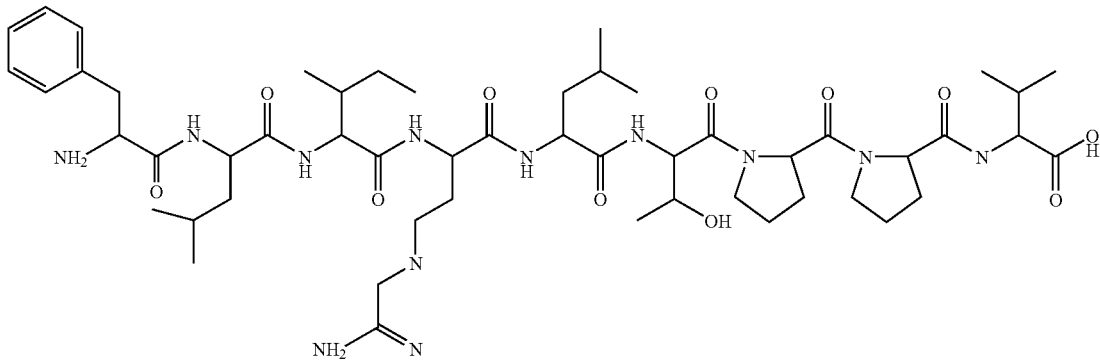

FLIRLTPPV (SEQ ID NO 13)

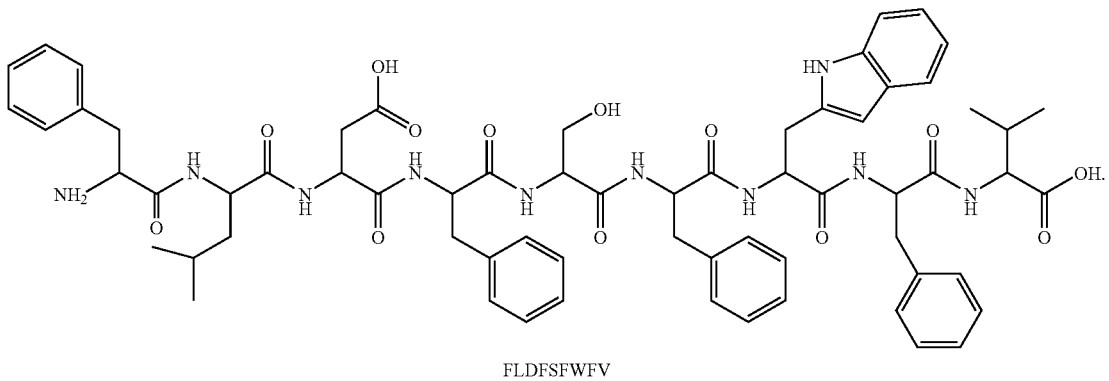

FLDFSFWFV

The present invention also provides compositions that exhibit enhancing binding to MHC molecules and are cross-reactive with and useful for modulating immune responses to the cognate native ligands and their corresponding native proteins.

This invention further provides compositions which are useful as components of anti-cancer vaccines and to expand immune effector cells that are specific for cancers characterized by expression of the CMV antigen.

In one embodiment, the altered ligands of the invention have comparable affinity for MHC binding as the native ligand. It has been demonstrated that peptide:MHC class I binding properties correlate with immunogenicity (Sette A. et al. (1994) J. Immunol. 153(12):5586-5592; van der Burg S. H. et al. (1996) J. Immunol. 156:3308-3314). In a preferred embodiment, altered ligands of the invention bind to a TCR with a higher affinity than of that the "natural" ligand. Comparative binding of the native and altered ligands of the invention to an MHC class 1 molecule can be measured by methods that are known in the art and include, but are not limited to, calculating the affinity based on an algorithm (see, for example, Parker et al. (1992) J. Immunol. 149:3580-3587) and experimentally determining binding affinity (see, for example, Tan et al. (1997) J. Immunol. Meth. 209(1):25-36). For example, the relative binding of a peptide to a class I molecule can be measured on the basis of binding of a radiolabeled standard peptide to detergent-solubilized MHC molecules, using various concentrations of test peptides (e.g., ranging from 100 mM to 1 nM). MHC class I heavy chain and β2-microglobulin are coincubated with a fixed concentration (e.g., 5 nM) radiolabeled standard (control) peptide and various concentrations of a test peptide for a suitable period of time (e.g., 2 hours to 72 hours) at room temperature in the presence of a mixture of protease inhibitors. A control tube contains standard peptide and MHC molecules, but no test peptide. The percent MHC-bound radioactivity is determined by gel filtration. The $IC_{50}$ (concentration of test peptide which results in 50% inhibition of binding of control peptide) is calculated for each peptide. Additional methods for determining binding affinity to a TCR are known in the art and include, but are not limited to, those described in al-Ramadi et al. (1992) J. Immunol. 155(2):662-673; and Zuegel et al. (1998) J. Immunol. 161(4):1705-1709.

In another embodiment, the altered ligands of the invention elicit comparable antigen-specific T cell activation relative to their native ligand counterpart. In a preferred embodiment, altered ligands of the invention elicit a stronger antigen-specific T cell activation relative to their native ligand counterpart. Methods for determining immunogenicity of invention ligands are known in the art and are further described herein.

In one embodiment, compositions of the invention comprise two or more immunogenic ligands of the invention. In one aspect, such compositions may comprise two or more copies of a single ligand. In another aspect, such compositions may comprise two or more ligands, wherein each ligand of said two or more ligands is distinct from all other ligands in said composition. In one embodiment, the two or more immunogenic ligands are covalently linked.

The present invention also provides novel synthetic antigenic peptides designed for enhancing binding to MHC molecules and useful for modulating immune responses to the synthetic peptide epitope and the corresponding native peptides from which they are derived. The synthetic antigenic peptide epitope sequences of the present invention differ from their natural counterparts in that they contain alterations in amino acid sequence, relative to the native sequence, in the MHC Class I binding domain which is designed to confer tighter binding to the MHC. They further contain mutations in the putative T cell receptor-binding domain designed to increase affinity for the T cell antigen receptor. These differences from the native sequence are designed to confer advantages in the methods of the present invention over the native sequence, in that the synthetic antigenic peptide epitopes of the invention will have enhanced immunomodulatory properties.

This invention provides novel, synthetic antigenic peptide sequences, which are useful as components of anti-viral vaccines and to expand immune effector cells that are specific for viral infections characterized by expression of the CMV antigen pp65. The peptides, FLLPMIATV (SEQ ID NO:3), FLLWDWPFV (SEQ ID NO:5), FLFTRFMRV (SEQ ID NO:7), FLPHPGWLV (SEQ ID NO:9), FLIRLTPPV (SEQ ID NO:11), and FLDFSFWFV (SEQ ID NO:13) differ from the natural CMV epitope NLVPMVATV (SEQ ID NO:2) in two ways: (1) they contain mutations in the putative HLA-A2 binding domain (specifically amino acid residue 1) conferring tighter binding to the MHC, and (2) they contain mutations in the putative T cell receptor-binding domain (amino acid residues 3-8) resulting in an increased avidity for the T cell receptor.

Binding of synthetic antigenic peptide of the invention to an MHC Class I molecule can be measured by methods that are known in the art and include, but are not limited to, calculating the affinity based on an algorithm (see, for example, Parker et al. (1992) J. Immunol. 149:3580-3587); and experimentally determining binding affinity (see, for example, Tan et al. (1997) J. Immunol. Meth. 209(1):25-36). For example, the relative binding of a peptide to a Class I molecule can be measured on the basis of binding of a radiolabeled standard peptide to detergent-solubilized MHC molecules, using various concentrations of test peptides (e.g., ranging from 100 mM to 1 nM). MHC Class I heavy chain and $\beta$2-microglobulin are coincubated with a fixed concentration (e.g., 5 nM) radiolabeled standard (control) peptide and various concentrations of a test peptide for a suitable period of time (e.g., 2 hours to 72 hours) at room temperature in the presence of a mixture of protease inhibitors. A control tube contains standard peptide and MHC molecules, but no test peptide. The percent MHC-bound radioactivity is determined by gel filtration. The $IC_{50}$ (concentration of test peptide which results in 50% inhibition of binding of control peptide) is calculated for each peptide.

Synthetic peptides of the invention are designed to bind to a TCR with a higher affinity than of that the "natural" sequence. Methods for determining binding affinity to a TCR are known in the art and include, but are not limited to, those described in al-Ramadi et al. (1992) J. Immunol. 155(2):662-673; and Zuegel et al. (1998) J. Immunol. 161(4):1705-1709.

Further encompassed by the term "synthetic antigenic peptide" are multimers (concatemers) of a synthetic antigenic peptide of the invention, optionally including intervening amino acid sequences as well as polypeptides comprising the sequences FLLPMIATV (SEQ ID NO:3), FLLWDWPFV (SEQ ID NO:5), FLFTRFMRV (SEQ ID NO:7), FLPHPGWLV (SEQ ID NO:9), FLIRLTPPV (SEQ ID NO:11) and FLDFSFWFV (SEQ ID NO:13). The invention also provides polypeptides comprising these sequences wherein the polypeptides are preferentially recognized by CMV antigen pp65 specific cytotoxic T lymphocytes.

Polypeptides comprising the peptide sequences of the invention can be prepared by altering the sequence of polynucleotides that encode the native CMV antigen pp65 polypeptide sequence. This is accomplished by methods of recombinant DNA technology well know to those skilled in the art. For example, site directed mutagenesis can be performed on recombinant polynucleotides encoding the native CMV antigen pp65 sequence to introduce changes in the polynucleotide sequence so that the altered polynucleotide encodes the peptides of the invention.

The proteins and polypeptides of this invention can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

Alternatively, the proteins and polypeptides can be obtained by well-known recombinant methods as described herein using the host cell and vector systems described below.

Peptide Analogues

It is well know to those skilled in the art that modifications can be made to the peptides of the invention to provide them with altered properties. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Peptides of the invention can be modified to include unnatural amino acids. Thus, the peptides may comprise D-amino acids, a combination of D- and L-amino acids, and various "designer" amino acids (e.g., $\beta$-methyl amino acids, C-$\alpha$-methyl amino acids, and N-$\alpha$-methyl amino acids, etc.) to convey special properties to peptides. Additionally, by assigning specific amino acids at specific coupling steps, peptides with $\alpha$-helices $\beta$ turns, $\beta$ sheets, $\gamma$-turns, and cyclic peptides can be generated. Generally, it is believed that $\alpha$-helical secondary structure or random secondary structure is preferred.

In a further embodiment, subunits of peptides that confer useful chemical and structural properties will be chosen. For example, peptides comprising D-amino acids will be resistant to L-amino acid-specific proteases in vivo. Modified compounds with D-amino acids may be synthesized with the amino acids aligned in reverse order to produce the peptides of the invention as retro-inverso peptides. In addition, the present invention envisions preparing peptides that have better defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2NH$—$R_2$, where $R_1$, and $R_2$ are amino acid residues or sequences. A reduced peptide bond may be introduced as a dipeptide subunit. Such a molecule would be resistant to peptide bond hydrolysis, e.g., protease activity. Such molecules would provide ligands with unique function and activity, such as extended half-lives in vivo due to resistance to metabolic breakdown, or protease activity. Furthermore, it is well known that in certain systems constrained peptides show enhanced functional activity (Hruby (1982) Life Sciences 31:189-199 and Hruby et al. (1990) Biochem J. 268:249-262); the present invention provides a method to produce a constrained peptide that incorporates random sequences at all other positions.

Non-Classical Amino Acids that Induce Conformational Constraints.

The following non classical amino acids may be incorporated in the peptides of the invention in order to introduce particular conformational motifs: 1,2,3,4-tetrahydroisoquinoline-3-carboxylate (Kazmierski et al. (1991) J. Am. Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby (1991) Tetrahedron Lett. 32(41):5769-5772); 2-aminotetrahydronaphthalene-2-carboxylic acid (Landis (1989) Ph.D. Thesis, University of Arizona); hydroxy-1,2,3,4-tetrahydroisoquinoline-3-carboxylate (Miyake et al. (1984) J. Takeda Res. Labs. 43:53-76) histidine isoquinoline carboxylic acid (Zechel et al. (1991) Int. J. Pep. Protein Res. 38(2): 131-138); and HIC (histidine cyclic urea), (Dharanipragada et al. (1993) Int. J. Pep. Protein Res. 42(1):68-77) and ((1992) Acta. Cryst., Crystal Struc. Comm. 48(IV):1239-1241).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al. (1985) J. Org. Chem. 50:5834-5838); β-sheet inducing analogs (Kemp et al. (1988) Tetrahedron Lett. 29:5081-5082); β-turn inducing analogs (Kemp et al. (1988) Tetrahedron Lett. 29:5057-5060); α-helix inducing analogs (Kemp et al. (1988) Tetrahedron Lett. 29:4935-4938); γ-turn inducing analogs (Kemp et al. (1989) J. Org. Chem. 54:109:115); analogs provided by the following references: Nagai and Sato (1985) Tetrahedron Lett. 26:647-650; and DiMaio et al. (1989) J. Chem. Soc. Perkin Trans. p. 1687; a Gly-Ala turn analog (Kahn et al. (1989) Tetrahedron Lett. 30:2317); amide bond isostere (Jones et al. (1988) Tetrahedron Lett. 29(31): 3853-3856); tetrazol (Zabrocki et al. (1988) J. Am. Chem. Soc. 110:5875-5880); DTC (Samanen et al. (1990) Int. J. Protein Pep. Res. 35:501:509); and analogs taught in Olson et al. (1990) J. Am. Chem. Sci. 112:323-333 and Garvey et al. (1990) J. Org. Chem. 55(3):936-940. Conformationally restricted mimetics of beta turns and beta bulges, and peptides containing them, are described in U.S. Pat. No. 5,440,013, issued Aug. 8, 1995 to Kahn.

A synthetic antigenic peptide epitope of the invention can be used in a variety of formulations, which may vary depending on the intended use.

A synthetic antigenic peptide epitope of the invention can be covalently or non-covalently linked (complexed) to various other molecules, the nature of which may vary depending on the particular purpose. For example, a peptide of the invention can be covalently or non-covalently complexed to a macromolecular carrier, including, but not limited to, natural and synthetic polymers, proteins, polysaccharides, polypeptides (amino acids), polyvinyl alcohol, polyvinyl pyrrolidone, and lipids. A peptide can be conjugated to a fatty acid, for introduction into a liposome. U.S. Pat. No. 5,837,249. A synthetic peptide of the invention can be complexed covalently or non-covalently with a solid support, a variety of which are known in the art. A synthetic antigenic peptide epitope of the invention can be associated with an antigen-presenting matrix with or without co-stimulatory molecules, as described in more detail below.

Examples of protein carriers include, but are not limited to, superantigens, serum albumin, tetanus toxoid, ovalbumin, thyroglobulin, myoglobulin, and immunoglobulin.

Peptide-protein carrier polymers may be formed using conventional cross-linking agents such as carbodimides. Examples of carbodimides are 1-cyclohexyl-3-(2-morpholinyl-(4-ethyl) carbodiimide (CMC), 1-ethyl-3-(3-dimethylaminopropyl) carbodiimide (EDC) and 1-ethyl-3-(4-azonia-44-dimethylpentyl) carbodiimide.

Examples of other suitable cross-linking agents are cyanogen bromide, glutaraldehyde and succinic anhydride. In general, any of a number of homo-bifunctional agents including a homo-bifunctional aldehyde, a homo-bifunctional epoxide, a homo-bifunctional imido-ester, a homo-bifunctional N-hydroxysuccinimide ester, a homo-bifunctional maleimide, a homo-bifunctional alkyl halide, a homo-bifunctional pyridyl disulfide, a homo-bifunctional aryl halide, a homo-bifunctional hydrazide, a homo-bifunctional diazonium derivative and a homo-bifunctional photoreactive compound may be used. Also included are hetero-bifunctional compounds, for example, compounds having an amine-reactive and a sulfhydryl-reactive group, compounds with an amine-reactive and a photoreactive group and compounds with a carbonyl-reactive and a sulfhydryl-reactive group.

Specific examples of such homo-bifunctional cross-linking agents include the bifunctional N-hydroxysuccinimide esters dithiobis(succinimidylpropionate), disuccinimidyl suberate, and disuccinimidyl tartarate; the bifunctional imido-esters dimethyl adipimidate, dimethyl pimelimidate, and dimethyl suberimidate; the bifunctional sulfhydryl-reactive crosslinkers 1,4-di-[3'-(2'-pyridyldithio) propion-amido] butane, bismaleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butanediol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), NIN'-hexamethylene-bis(iodoacetamide), NIN'-undecamethylene-bis(iodoacetamide), as well as benzylhalides and halomustards, such as al a'-diiodo-p-xylene sulfonic acid and tri(2-chloroethyl)amine, respectively.

Examples of common hetero-bifunctional cross-linking agents that may be used to effect the conjugation of proteins to peptides include, but are not limited to, SMCC (succinimidyl-4-(N-maleimidomethyl)cyclohexane-1-carboxylate), MBS (m-maleimidobenzoyl-N-hydroxysuccinimide ester), SIAB (N-succinimidyl(4-iodoacetyl)aminobenzoate), SMPB (succinimidyl-4-(p-maleimidophenyl)butyrate), GMBS (N-(γ-maleimidobutyryloxy)succinimide ester), MPBH (4-(4-N-maleimidophenyl) butyric acid hydrazide), M2C2H (4-(N-maleimidomethyl)cyclohexane-1-carboxyl-hydrazide), SMPT (succinimidyloxycarbonyl-á-methyl-á-(2-pyridyldithio)toluene), and SPDP (N-succinimidyl 3-(2-pyridyldithio)propionate).

Cross-linking may be accomplished by coupling a carbonyl group to an amine group or to a hydrazide group by reductive amination.

Peptides of the invention also may be formulated as non-covalent attachment of monomers through ionic, adsorptive, or biospecific interactions. Complexes of peptides with highly positively or negatively charged molecules may be done through salt bridge formation under low ionic strength environments, such as in deionized water. Large complexes can be created using charged polymers such as poly-(L- glutamic acid) or poly-(L-lysine) which contain numerous negative and positive charges, respectively. Adsorption of peptides may be done to surfaces such as microparticle latex beads or to other hydrophobic polymers, forming non-covalently associated peptide-superantigen complexes effectively mimicking cross-linked or chemically polymerized protein. Finally, peptides may be non-covalently linked through the use of biospecific interactions between other molecules. For instance, utilization of the strong affinity of biotin for proteins such as avidin or streptavidin or their derivatives could be used to form peptide complexes. These biotin-binding proteins contain four binding sites that can interact with biotin in solution or be covalently attached to another molecule. Wilchek (1988) Anal. Biochem. 171:1-32. Peptides can be modified to possess biotin groups using common biotinylation reagents such as the N-hydroxysuccinimidyl ester of D-biotin (NHS-biotin) which reacts with available amine groups on the protein. Biotinylated peptides then can be incubated with avidin or streptavidin to create large complexes. The molecular mass of such polymers can be regulated through careful control of the molar ratio of biotinylated peptide to avidin or streptavidin.

Also provided by this application are the peptides and polypeptides described herein conjugated to a detectable agent for use in the diagnostic methods. For example, detectably labeled peptides and polypeptides can be bound to a column and used for the detection and purification of antibodies. They also are useful as immunogens for the production of antibodies, as described below.

The peptides of this invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils. When used to prepare antibodies, the carriers also can include an adjuvant that is useful to non-specifically augment a specific immune response. A skilled artisan can easily determine whether an adjuvant is required and select one. However, for the purpose of illustration only, suitable adjuvants include, but are not limited to, Freund's Complete and Incomplete, mineral salts and polynucleotides.

This invention further provides polynucleotides (SEQ ID NOs: 4, 6, 8, 10, 12, 14) encoding polypeptides comprising the sequences FLLPMIATV (SEQ ID NO:3), FLLWDWPFV (SEQ ID NO:5), FLFTRFMRV (SEQ ID NO:7), FLPHPGWLV (SEQ ID NO:9), FLIRLTPPV (SEQ ID NO:11) and FLDFSFWFV (SEQ ID NO:13), and the complements of these polynucleotides. As used herein, the term "polynucleotide" encompasses DNA, RNA and nucleic acid mimetics. In addition to the sequences shown in SEQ ID NOs: 4, 6, 8, 10, 12, and 14 or their complements, this invention also provides the anti-sense polynucleotide stand, e.g., antisense RNA to these sequences or their complements. One can obtain an antisense RNA using the sequences provided in SEQ ID NOs: 4, 6, 8, 10, 12, and 14 and the methodology described in Vander Krol, et al. (1988) BioTechniques 6:958.

The polynucleotides of this invention can be replicated using PCR. PCR technology is the subject matter of U.S. Pat. Nos. 4,683,195; 4,800,159; 4,754,065; and 4,683,202 and described in PCR: THE POLYMERASE CHAIN REACTION (Mullis et al. eds, Birkhauser Press, Boston (1994)) and references cited therein.

Alternatively, one of skill in the art can use the sequences provided herein and a commercial DNA synthesizer to replicate the DNA. Accordingly, this invention also provides a process for obtaining the polynucleotides of this invention by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

RNA can be obtained by first inserting a DNA polynucleotide into a suitable host cell. The DNA can be inserted by any appropriate method, e.g., by the use of an appropriate gene delivery vehicle (e.g., liposome, plasmid or vector) or by electroporation. When the cell replicates and the DNA is transcribed into RNA; the RNA can then be isolated using methods well known to those of skill in the art, for example, as set forth in Sambrook et al. (1989) supra. For instance, mRNA can be isolated using various lytic enzymes or chemical solutions according to the procedures set forth in Sambrook, et al. (1989) supra or extracted by nucleic-acid-binding resins following the accompanying instructions provided by manufactures.

Polynucleotides having at least 4 contiguous nucleotides, and more preferably at least 5 or 6 contiguous nucleotides and most preferably at least 10 contiguous nucleotides, and exhibiting sequence complementarity or homology to SEQ ID NOs: 3, 5, 7, 9, 11, and 13 find utility as hybridization probes.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. Preferably, a probe useful for detecting the aforementioned mRNA is at least about 80% identical to the homologous region of comparable size contained in the previously identified sequences identified by SEQ ID NOs: 2, 4, 6, 8, 10, 12, and 14 which correspond to previously characterized genes or in sequences identified in SEQ ID NOs: 2, 4, 6, 8, 10, 12, and 14. More preferably, the probe is 85% identical to the corresponding gene sequence after alignment of the homologous region; even more preferably, it exhibits 90% identity.

These probes can be used in radioassays (e.g. Southern and Northern blot analysis) to detect or monitor various cells or tissue containing these cells. The probes also can be attached to a solid support or an array such as a chip for use in high throughput screening assays for the detection of expression of the gene corresponding to one or more polynucleotide(s) of this invention. Accordingly, this invention also provides at least one probe as defined above of the transcripts identified as SEQ ID NOs: 1, 4, 6, 8, 10, 12, and 14 or the complement of one of these sequences, attached to a solid support for use in high throughput screens.

The polynucleotides of the present invention also can serve as primers for the detection of genes or gene transcripts that are expressed in APC, for example, to confirm transduction of the polynucleotides into host cells. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of E. coli DNA polymerase, and reverse transcriptase. A preferred length of the primer is the same as that identified for probes, above.

The invention further provides the isolated polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are well known in the art and commercially available. For general methodology and cloning strategies, see GENE EXPRESSION TECHNOLOGY (Goeddel ed., Academic Press, Inc. (1991)) and references cited therein and VECTORS: ESSENTIAL DATA SERIES (Gacesa and Ramji, eds., John Wiley & Sons, N.Y. (1994)), which contains maps, functional properties, commercial suppliers and a reference to GenEMBL accession numbers for various suitable vectors. Preferably, these vectors are capable of transcribing RNA in vitro or in vivo.

Expression vectors containing these nucleic acids are useful to obtain host vector systems to produce proteins and polypeptides. It is implied that these expression vectors must be replicable in the host organisms either as episomes or as an integral part of the chromosomal DNA. Suitable expression vectors include plasmids, viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells constructed using well known methods. See Sambrook, et al. (1989) supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; DEAE-dextran; electroporation; or microinjection. See Sambrook et al. (1989) supra for this methodology. Thus, this invention also provides a host cell, e.g. a mammalian cell, an animal cell (rat or mouse), a human cell, or a prokaryotic cell such as a bacterial cell, containing a polynucleotide encoding a protein or polypeptide or antibody.

The present invention also provides delivery vehicles suitable for delivery of a polynucleotide of the invention into cells (whether in vivo, ex vivo, or in vitro). A polynucleotide of the invention can be contained within a cloning or expression vector. These vectors (especially expression vectors) can in turn be manipulated to assume any of a number of forms which may, for example, facilitate delivery to and/or entry into a cell.

When the vectors are used for gene therapy in vivo or ex vivo, a pharmaceutically acceptable vector is preferred, such as a replication-incompetent retroviral or adenoviral vector. Pharmaceutically acceptable vectors containing the nucleic acids of this invention can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller A. D. et al. (1989) BioTechniques 7:980-990). The methodology of using replication-incompetent retroviruses for retroviral-mediated gene transfer of gene markers is well established (Correll et al. (1989) Proc. Natl. Acad. Sci. USA 86:8912; Bordignon (1989) Proc. Natl. Acad. Sci. USA 86(17):6748-6752; Culver K. (1991) Proc. Natl. Acad. Sci. USA 88:3155; and Rill D. R. (1992) Blood 79(10):2694-2700).

These isolated host cells containing the polynucleotides of this invention are useful for the recombinant replication of the polynucleotides and for the recombinant production of peptides. Alternatively, the cells may be used to induce an immune response in a subject in the methods described herein. When the host cells are antigen presenting cells, they can be used to expand a population of immune effector cells such as tumor infiltrating lymphocytes which in turn are useful in adoptive immunotherapies.

Also provided by this invention is an antibody capable of specifically forming a complex with the polypeptides of this invention. The term "antibody" includes polyclonal antibodies and monoclonal antibodies. The antibodies include, but are not limited to mouse, rat, and rabbit or human antibodies. The antibodies are useful to identify and purify polypeptides and APCs expressing the polypeptides.

Laboratory methods for producing polyclonal antibodies and monoclonal antibodies, as well as deducing their corresponding nucleic acid sequences, are known in the art, see Harlow and Lane (1988) supra and Sambrook et al. (1989) supra. The monoclonal antibodies of this invention can be biologically produced by introducing protein or a fragment thereof into an animal, e.g., a mouse or a rabbit. The antibody producing cells in the animal are isolated and fused with myeloma cells or hetero-myeloma cells to produce hybrid cells or hybridomas. Accordingly, the hybridoma cells producing the monoclonal antibodies of this invention also are provided.

Thus, using the protein or fragment thereof, and well known methods, one of skill in the art can produce and screen the hybridoma cells and antibodies of this invention for antibodies having the ability to bind the proteins or polypeptides.

If a monoclonal antibody being tested binds with the protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Meth. 74:307.

This invention also provides biological active fragments of the polyclonal and monoclonal antibodies described above. These "antibody fragments" retain some ability to selectively bind with its antigen or immunogen. Such antibody fragments can include, but are not limited to:

Fab,
Fab',
F(ab')$_2$,
Fv, and
SCA.

A specific example of "a biologically active antibody fragment" is a CDR region of the antibody. Methods of making these fragments are known in the art, see for example, Harlow and Lane (1988) supra.

The antibodies of this invention also can be modified to create chimeric antibodies and humanized antibodies (Oi et al. (1986) BioTechniques 4(3):214). Chimeric antibodies are those in which the various domains of the antibodies' heavy and light chains are coded for by DNA from more than one species.

The isolation of other hybridomas secreting monoclonal antibodies with the specificity of the monoclonal antibodies of the invention can also be accomplished by one of ordinary skill in the art by producing anti-idiotypic antibodies (Herlyn et al. (1986) Science 232:100). An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

As used in this invention, the term "epitope" is meant to include any determinant having specific affinity for the monoclonal antibodies of the invention. Epitopic determinants usually consist of chemically active surface groupings of molecules such as amino acids or sugar side chains and usually have specific three dimensional structural characteristics, as well as specific charge characteristics.

The antibodies of this invention can be linked to a detectable agent or label. There are many different labels and methods of labeling known to those of ordinary skill in the art.

The coupling of antibodies to low molecular weight haptens can increase the sensitivity of the assay. The haptens can then be specifically detected by means of a second reaction. For example, it is common to use haptens such as biotin, which reacts avidin, or dinitropherryl, pyridoxal, and fluorescein, which can react with specific anti-hapten antibodies. See Harlow and Lane (1988) supra.

The monoclonal antibodies of the invention also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

Compositions containing the antibodies, fragments thereof or cell lines which produce the antibodies are encompassed by this invention. When these compositions are to be used pharmaceutically, they are combined with a pharmaceutically acceptable carrier.

In another embodiment the present invention provides a method of inducing an immune response comprising delivering the compounds and compositions of the invention in the context of an MHC molecule. Thus, the polypeptides of this invention can be pulsed into antigen presenting cells using the methods described herein. Antigen-presenting cells, include, but are not limited to dendritic cells (DCs), monocytes/macrophages, B lymphocytes or other cell type(s) expressing the necessary MHC/co-stimulatory molecules. The methods described below focus primarily on DCs which are the most potent, preferred APCs. These host cells containing the polypeptides or proteins are further provided.

Isolated host cells which present the polypeptides of this invention in the context of MHC molecules are further useful to expand and isolate a population of educated, antigen-specific immune effector cells. The immune effector cells, e.g., cytotoxic T lymphocytes, are produced by culturing naïve immune effector cells with antigen-presenting cells which present the polypeptides in the context of MHC molecules on the surface of the APCs. The population can be purified using methods known in the art, e.g., FACS analysis or ficoll gradient. The methods to generate and culture the immune effector cells as well as the populations produced thereby also are the inventor's contribution and invention. Pharmaceutical compositions comprising the cells and pharmaceutically acceptable carriers are useful in adoptive immunotherapy. Prior to administration in vivo, the immune effector cells are screened in vitro for their ability to lyse CMV pp65 antigen-expressing tumor cells.

In one embodiment, the immune effector cells and/or the APCs are genetically modified. Using standard gene transfer, genes coding for co-stimulatory molecules and/or stimulatory cytokines can be inserted prior to, concurrent to or subsequent to expansion of the immune effector cells.

This invention also provides methods of inducing an immune response in a subject, comprising administering to the subject an effective amount of the polypeptides described above under the conditions that induce an immune response to the polypeptide. The polypeptides can be administered in formulations or as polynucleotides encoding the polypeptides. The polynucleotides can be administered in a gene delivery vehicle or by inserting into a host cell which in turn recombinantly transcribes, translates and processed the encoded polypeptide. Isolated host cells containing the polynucleotides of this invention in a pharmaceutically acceptable carrier can therefore combined with appropriate and effective amount of an adjuvant, cytokine or co-stimulatory molecule for an effective vaccine regimen. In one embodiment, the host cell is an APC such as a dendritic cell. The host cell can be further modified by inserting of a polynucleotide coding for an effective amount of either or both a cytokine and/or a co-stimulatory molecule.

The methods of this invention can be further modified by co-administering an effective amount of a cytokine or co-stimulatory molecule to the subject.

This invention also provides compositions containing any of the above-mentioned proteins, polypeptides, polynucleotides, vectors, cells, antibodies and fragments thereof, and an acceptable solid or liquid carrier. When the compositions are used pharmaceutically, they are combined with a "pharmaceutically acceptable carrier" for diagnostic and therapeutic use. These compositions also can be used for the preparation of medicaments for the diagnosis and treatment of diseases such as cancer.

The following materials and methods are intended to illustrate, but not limit this invention and to illustrate how to make and use the inventions described above.

Materials and Methods

Production of the Polypeptides of the Invention

Most preferably, isolated peptides of the present invention can be synthesized using an appropriate solid state synthetic procedure. Steward and Young, SOLID PHASE PEPTIDE SYNTHESIS, Freemantle, San Francisco, Calif. (1968). A preferred method is the Merrifield process. See, Merrifield (1967) Recent Progress in Hormone Res. 23:451. The antigenic activity of these peptides may conveniently be tested using, for example, the assays as described herein.

Once an isolated peptide of the invention is obtained, it may be purified by standard methods including chromatography (e.g., ion exchange, affinity, and sizing column chromatography), centrifugation, differential solubility, or by any other standard technique for protein purification. For immuno-affinity chromatography, an epitope may be isolated by binding it to an affinity column comprising antibodies that were raised against that peptide, or a related peptide of the invention, and were affixed to a stationary support.

Alternatively, affinity tags such as hexa-His (Invitrogen), Maltose binding domain (New England Biolabs), influenza coat sequence (Kolodziej et al. (1991) Meth. Enzymol. 194: 508-509), and glutathione-S-transferase can be attached to the peptides of the invention to allow easy purification by passage over an appropriate affinity column. Isolated peptides can also be physically characterized using such techniques as proteolysis, nuclear magnetic resonance, and x-ray crystallography.

Also included within the scope of the invention are antigenic peptides that are differentially modified during or after translation, e.g., by phosphorylation, glycosylation, cross-linking, acylation, proteolytic cleavage, linkage to an antibody molecule, membrane molecule or other ligand, (Ferguson et al. (1988) Ann. Rev. Biochem. 57:285-320).

Isolation, Culturing and Expansion of APCs, Including Dendritic Cells

The following is a brief description of two fundamental approaches for the isolation of APC. These approaches involve (1) isolating bone marrow precursor cells (CD34$^+$) from blood and stimulating them to differentiate into APC; or (2) collecting the precommitted APCs from peripheral blood. In the first approach, the patient must be treated with cytokines such as GM-CSF to boost the number of circulating CD34$^+$ stem cells in the peripheral blood.

The second approach for isolating APCs is to collect the relatively large numbers of precommitted APCs already circulating in the blood. Previous techniques for isolating committed APCs from human peripheral blood have involved combinations of physical procedures such as metrizamide gradients and adherence/non-adherence steps (Freudenthal P. S. et al. (1990) Proc. Natl. Acad. Sci. USA 87:7698-7702); Percoll gradient separations (Mehta-Damani et al. (1994) J. Immunol. 153:996-1003); and fluorescence activated cell sorting techniques (Thomas R. et al. (1993) J. Immunol. 151:6840-6852).

One technique for separating large numbers of cells from one another is known as countercurrent centrifugal elutriation (CCE). In this technique, cells are subject to simultaneous centrifugation and a washout stream of buffer that is constantly increasing in flow rate. The constantly increasing countercurrent flow of buffer leads to fractional cell separations that are largely based on cell size.

In one aspect of the invention, the APC are precommitted or mature dendritic cells which can be isolated from the white blood cell fraction of a mammal, such as a murine, simian or a human (See, e.g., WO 96/23060). The white blood cell fraction can be from the peripheral blood of the mammal. This method includes the following steps: (a) providing a white blood cell fraction obtained from a mammalian source by methods known in the art such as leukophoresis; (b) separating the white blood cell fraction of step (a) into four or more subfractions by countercurrent centrifugal elutriation; (c) stimulating conversion of monocytes in one or more fractions from step (b) to dendritic cells by contacting the cells with calcium ionophore, GM-CSF and IL-13 or GM-CSF and IL-4, (d) identifying the dendritic cell-enriched fraction from step (c); and (e) collecting the enriched fraction of step (d), preferably at about 4° C. One way to identify the dendritic cell-enriched fraction is by fluorescence-activated cell sorting. The white blood cell fraction can be treated with calcium ionophore in the presence of other cytokines, such as recombinant (rh) rhIL-12, rhGM-CSF, or rhIL-4. The cells of the white blood cell fraction can be washed in buffer and suspended in Ca$^{++}$/Mg$^{++}$ free media prior to the separating step. The white blood cell fraction can be obtained by leukapheresis. The dendritic cells can be identified by the presence of at least one of the following markers: HLA-DR, HLA-DQ, or B7.2, and the simultaneous absence of the following markers: CD3, CD14, CD16, 56, 57, and CD 19, 20. Monoclonal antibodies specific to these cell surface markers are commercially available.

More specifically, the method requires collecting an enriched collection of white cells and platelets from leukapheresis that is then further fractionated by countercurrent centrifugal elutriation (CCE) (Abrahamsen T. G. et al. (1991) J. Clin. Apheresis. 6:48-53). Cell samples are placed in a special elutriation rotor. The rotor is then spun at a constant speed of, for example, 3000 rpm. Once the rotor has reached the desired speed, pressurized air is used to control the flow rate of cells. Cells in the elutriator are subjected to simultaneous centrifugation and a washout stream of buffer that is constantly increasing in flow rate. This results in fractional cell separations based largely but not exclusively on differences in cell size.

Quality control of APC and more specifically DC collection and confirmation of their successful activation in culture is dependent upon a simultaneous multi-color FACS analysis technique which monitors both monocytes and the dendritic cell subpopulation as well as possible contaminant T lymphocytes. It is based upon the fact that DCs do not express the following markers: CD3 (T cell); CD14 (monocyte); CD16, 56, 57 (NK/LAK cells); CD19, 20 (B cells). At the same time, DCs do express large quantities of HLA-DR, significant HLA-DQ and B7.2 (but little or no B7.1) at the time they are circulating in the blood (in addition they express Leu M7 and M9, myeloid markers which are also expressed by monocytes and neutrophils).

When combined with a third color reagent for analysis of dead cells, propidium iodide (PI), it is possible to make positive identification of all cell subpopulations (see Table 1):

TABLE 1

FACS analysis of fresh peripheral cell subpopulations

|  | Color #1 Cocktail 3/14/16/19/20/56/57 | Color #2 HLA-DR | Color #3 PI |
|---|---|---|---|
| Live Dendritic cells | Negative | Positive | Negative |
| Live Monocytes | Positive | Positive | Negative |
| Live Neutrophils | Negative | Negative | Negative |
| Dead Cells | Variable | Variable | Positive |

Additional markers can be substituted for additional analysis:

Color #1: CD3 alone, CD14 alone, etc.; Leu M7 or Leu M9; anti-Class I, etc.

Color #2: HLA-DQ, B7.1, B7.2, CD25 (IL2r), ICAM, LFA-3, etc.

The goal of FACS analysis at the time of collection is to confirm that the DCs are enriched in the expected fractions, to monitor neutrophil contamination, and to make sure that appropriate markers are expressed. This rapid bulk collection of enriched DCs from human peripheral blood, suitable for clinical applications, is absolutely dependent on the analytic FACS technique described above for quality control. If need be, mature DCs can be immediately separated from monocytes at this point by fluorescent sorting for "cocktail negative" cells. It may not be necessary to routinely separate DCs from monocytes because, as will be detailed below, the monocytes themselves are still capable of differentiating into DCs or functional DC-like cells in culture.

Once collected, the DC rich/monocyte APC fractions (usually 150 through 190) can be pooled and cryopreserved for future use, or immediately placed in short term culture.

Alternatively, others have reported a method for upregulating (activating) dendritic cells and converting monocytes to an activated dendritic cell phenotype. This method involves the addition of calcium ionophore to the culture media convert monocytes into activated dendritic cells. Adding the calcium ionophore A23187, for example, at the beginning of a 24-48 hour culture period resulted in uniform activation and dendritic cell phenotypic conversion of the pooled "monocyte plus DC" fractions: characteristically, the activated population becomes uniformly CD14 (Leu M3) negative, and upregulates HLA-DR, HLA-DQ, ICAM-1, B7.1, and B7.2. Furthermore, this activated bulk population functions as well on a small numbers basis as a further purified.

Specific combination(s) of cytokines have been used successfully to amplify (or partially substitute) for the activation/conversion achieved with calcium ionophore: these cytokines include but are not limited to purified or recombinant ("rh") rhGM-CSF, rhIL-2, and rhIL-4. Each cytokine when given alone is inadequate for optimal upregulation.

Presentation of Antigen to the APC

For purposes of immunization, the antigenic peptides (SEQ ID NOs: 3, 5, 7, 9, 11 and 13) can be delivered to antigen-presenting cells as protein/peptide or in the form of cDNA encoding the protein/peptide. Antigen-presenting cells (APCs) can consist of dendritic cells (DCs), monocytes/macrophages, B lymphocytes or other cell type(s) expressing the necessary MHC/co-stimulatory molecules. The methods described below focus primarily on DCs which are the most potent, preferred APCs.

Pulsing is accomplished in vitro/ex vivo by exposing APCs to the antigenic protein or peptide(s) of this invention. The protein or peptide(s) are added to APCs at a concentration of 1-10 μm for approximately 3 hours. Pulsed APCs can subsequently be administered to the host via an intravenous, subcutaneous, intranasal, intramuscular or intraperitoneal route of delivery.

Protein/peptide antigen can also be delivered in vivo with adjuvant via the intravenous, subcutaneous, intranasal, intramuscular or intraperitoneal route of delivery.

Paglia et al. (1996) J. Exp. Med. 183:317-322 has shown that APC incubated with whole protein in vitro were recognized by MHC class I-restricted CTLs, and that immunization of animals with these APCs led to the development of antigen-specific CTLs in vivo. In addition, several different techniques have been described which lead to the expression of antigen in the cytosol of APCs, such as DCs. These include (1) the introduction into the APCs of RNA isolated from tumor cells, (2) infection of APCs with recombinant vectors to induce endogenous expression of antigen, and (3) introduction of tumor antigen into the DC cytosol using liposomes. (See Boczkowski D. et al. (1996) J. Exp. Med. 184:465-472; Rouse et al. (1994) J. Virol. 68:5685-5689; and Nair et al. (1992) J. Exp. Med. 175:609-612).

Foster Antigen Presenting Cells

Foster antigen presenting cells are particularly useful as target cells. Foster APCs are derived from the human cell line 174×CEM.T2, referred to as T2, which contains a mutation in its antigen processing pathway that restricts the association of endogenous peptides with cell surface MHC class I molecules (Zweerink et al. (1993) J. Immunol. 150:1763-1771). This is due to a large homozygous deletion in the MHC class II region encompassing the genes TAP1, TAP2, LMP1, and LMP2, which are required for antigen presentation to MHC class I-restricted CD8$^+$ CTLs. In effect, only "empty" MHC class I molecules are presented on the surface of these cells. Exogenous peptide added to the culture medium binds to these MHC molecules provided that the peptide contains the allele-specific binding motif. These T2 cells are referred to herein as "foster" APCs. They can be used in conjunction with this invention to present antigen(s).

Transduction of T2 cells with specific recombinant MHC alleles allows for redirection of the MHC restriction profile. Libraries tailored to the recombinant allele will be preferentially presented by them because the anchor residues will prevent efficient binding to the endogenous allele.

High level expression of MHC molecules makes the APC more visible to the CTLs. Expressing the MHC allele of interest in T2 cells using a powerful transcriptional promoter (e.g., the CMV promoter) results in a more reactive APC (most likely due to a higher concentration of reactive MHC-peptide complexes on the cell surface).

Immunogenicity Assays.

The immunogenicity of invention ligands can be determined by well known methodologies including, but not limited to those exemplified below. In one embodiment, such methodology may be employed to compare an altered ligand of the invention with the corresponding native ligand. For example, an altered ligand may be considered "more active" if it compares favorably with the activity of the native ligand in any one of the following assays. For some purposes, one skilled in the art will select an immunogenic ligand which displays more activity than another immunogenic ligand, i.e., for treatment and/or diagnostic purposes. However, for some applications, the use of an immunogenic ligand which is comparable with the native ligand will be suitable. In other situations, it may be desirable to utilize an immunogenic ligand which is less active. It has been suggested that such levels of activity positively correlate with the level of immunogenicity.

$^{51}$Cr-release lysis assay. Lysis of peptide-pulsed $^{51}$Cr-labeled targets by antigen-specific T cells can be compared for target cells pulsed with either the native or altered ligands. Functionally enhanced ligands will show greater lysis of targets as a function of time. The kinetics of lysis as well as overall target lysis at a fixed timepoint (e.g., 4 hours) may be used to evaluate ligand performance. (Ware C. F. et al. (1983) J. Immunol. 131:1312).

Cytokine-release assay. Analysis of the types and quantities of cytokines secreted by T cells upon contacting ligand-pulsed targets can be a measure of functional activity. Cytokines can be measured by ELISA or ELISPOT assays to determine the rate and total amount of cytokine production. (Fujihashi K. et al. (1993) J. Immunol. Meth. 160:181; Tanguay S. and Killion J. J. (1994) Lymphokine Cytokine Res. 13:259).

In vitro T cell education. The ligands of the invention can be compared to the corresponding native ligand for the ability to elicit ligand-reactive T cell populations from normal donor or patient-derived PBMC. In this system, elicited T cells can be tested for lytic activity, cytokine-release, polyclonality, and cross-reactivity to the native ligand. (Parkhurst M. R. et al. (1996) J. Immunol. 157:2539).

Transgenic animal models. Immunogenicity can be assessed in vivo by vaccinating HLA transgenic mice with either the ligands of the invention or the native ligand and determining the nature and magnitude of the induced immune response. Alternatively, the hu-PBL-SCID mouse model allows reconstitution of a human immune system in a mouse by adoptive transfer of human PBL. These animals may be vaccinated with the ligands and analyzed for immune response as previously mentioned. (Shirai M. et al. (1995) J. Immunol. 154:2733; Mosier D. E. et al. (1993) Proc. Natl. Acad. Sci. USA 90:2443).

Proliferation. T cells will proliferate in response to reactive ligands. Proliferation can be monitored quantitatively by measuring, for example, $^3$H-thymidine uptake. (Caruso A. et al. (1997) Cytometry 27:71).

Tetramer staining. MHC tetramers can be loaded with individual ligands and tested for their relative abilities to bind to appropriate effector T cell populations. (Altman J. D. et al. (1996) Science 274(5284):94-96).

MHC Stabilization. Exposure of certain cell lines such as T2 cells to HLA-binding ligands results in the stabilization of MHC complexes on the cell surface. Quantitation of MHC complexes on the cell surface has been correlated with the affinity of the ligand for the HLA allele that is stabilized. Thus, this technique can determine the relative HLA affinity of ligand epitopes. (Stuber G. et al. (1995) Int. Immunol. 7:653).

MHC competition. The ability of a ligand to interfere with the functional activity of a reference ligand and its cognate T cell effectors is a measure of how well a ligand can compete for MHC binding. Measuring the relative levels of inhibition is an indicator of MHC affinity. (Feltkamp M. C. et al. (1995) Immunol. Lett. 47:1).

Primate models. A recently described non-human primate (chimpanzee) model system can be utilized to monitor in vivo immunogenicities of HLA-restricted ligands. It has been demonstrated that chimpanzees share overlapping MHC-ligand specificities with human MHC molecules thus allowing one to test HLA-restricted ligands for relative in vivo immunogenicity. (Bertoni R. et al. (1998) J. Immunol. 161: 4447).

Monitoring TCR Signal Transduction Events. Several intracellular signal transduction events (e.g., phosphorylation) are associated with successful TCR engagement by MHC-ligand complexes. The qualitative and quantitative analysis of these events have been correlated with the relative abilities of ligands to activate effector cells through TCR engagement. (Salazar E. et al. (2000) Int. J. Cancer 85:829; Isakov N. et al. (1995) J. Exp. Med. 181:375).

Expansion of Immune Effector Cells

The present invention makes use of these APCs to stimulate production of an enriched population of antigen-specific immune effector cells. The antigen-specific immune effector cells are expanded at the expense of the APCs, which die in the culture. The process by which naïve immune effector cells become educated by other cells is described essentially in Coulie (1997) Molec. Med. Today 3:261-268.

The APCs prepared as described above are mixed with naïve immune effector cells. Preferably, the cells may be cultured in the presence of a cytokine, for example IL-2. Because dendritic cells secrete potent immunostimulatory cytokines, such as IL-12, it may not be necessary to add supplemental cytokines during the first and successive rounds of expansion. In any event, the culture conditions are such that the antigen-specific immune effector cells expand (i.e., proliferate) at a much higher rate than the APCs. Multiple infusions of APCs and optional cytokines can be performed to further expand the population of antigen-specific cells.

In one embodiment, the immune effector cells are T cells. In a separate embodiment, the immune effector cells can be genetically modified by transduction with a transgene coding for example, IL-2, IL-11 or IL-13. Methods for introducing transgenes in vitro, ex vivo and in vivo are well known in the art. See Sambrook et al. (1989) supra.

Vectors Useful in Genetic Modifications

In general, genetic modifications of cells employed in the present invention are accomplished by introducing a vector containing a polypeptide or transgene encoding a heterologous or an altered antigen. A variety of different gene transfer vectors, including viral as well as non-viral systems can be used. Viral vectors useful in the genetic modifications of this invention include, but are not limited to adenovirus, adeno-associated virus vectors, retroviral vectors and adeno-retroviral chimeric vectors. APC and immune effector cells can be modified using the methods described below or by any other appropriate method known in the art.

Construction of Recombinant Adenoviral Vectors or Adeno-Associated Virus Vectors Adenovirus and adeno-associated virus vectors useful in the genetic modifications of this invention may be produced according to methods already taught in the art. See, e.g., Karlsson et al. (1986) EMBO J. 5:2377; Carter (1992) Curr. Op. Biotechnol. 3:533-539; Muzcyzka (1992) Current Top. Microbiol. Immunol. 158:97-129; GENE TARGETING: A PRACTICAL APPROACH (1992) ed. A. L. Joyner, Oxford University Press, NY). Several different approaches are feasible. Preferred is the helper-independent replication deficient human adenovirus system.

The recombinant adenoviral vectors based on the human adenovirus 5 (McGrory, W. J. et al. (1988) Virology 163:614-617) are missing essential early genes from the adenoviral genome (usually E1A/E1B), and are therefore unable to replicate unless grown in permissive cell lines that provide the missing gene products in trans. In place of the missing adenoviral genomic sequences, a transgene of interest can be cloned and expressed in cells infected with the replication deficient adenovirus. Although adenovirus-based gene transfer does not result in integration of the transgene into the host genome (less than 0.1% adenovirus-mediated transfections result in transgene incorporation into host DNA), and therefore is not stable, adenoviral vectors can be propagated in high titer and transfect non-replicating cells. Human 293 cells, which are human embryonic kidney cells transformed with adenovirus E1A/E1B genes, typify useful permissive cell lines. However, other cell lines which allow replication-deficient adenoviral vectors to propagate therein can be used, including HeLa cells.

Additional references describing adenovirus vectors and other viral vectors which could be used in the methods of the present invention include the following: Horwitz M. S. ADENOVIRIDAE AND THEIR REPLICATION, in Fields B. et al. (eds.) VIROLOGY, Vol. 2, Raven Press New York, pp. 1679-1721 (1990); Graham F. et al. pp. 109-128 in METHODS IN MOLECULAR BIOLOGY, Vol. 7: GENE TRANSFER AND EXPRESSION PROTOCOLS, Murray E. (ed.) Humana Press, Clifton, N.J. (1991); Miller N. et al. (1995) FASEB J. 9:190-199; Schreier H. (1994) Pharmaceutica Acta Helvetiae 68:145-159; Schneider and French (1993) Circulation 88:1937-1942; Curiel D. T. et al. (1992) Hum. Gene Ther. 3:147-154; Graham F. L. et al. WO 95/00655 (5 Jan. 1995); Falck-Pedersen E. S. WO 95/16772 (22 Jun. 1995); Denefle P. et al. WO 95/23867 (8 Sep. 1995); Haddada H. et al. WO 94/26914 (24 Nov. 1994); Perricaudet M. et al. WO 95/02697 (26 Jan. 1995); Zhang W. et al. WO 95/25071 (12 Oct. 1995). A variety of adenovirus plasmids are also available from commercial sources, including, e.g., Microbix Biosystems of Toronto, Ontario (see, e.g., Microbix Product Information Sheet Plasmids for Adenovirus Vector Construction, 1996). See also, the papers by Vile et al. (1997) Nature Biotechnology 15:840-841; and Feng et al. (1997) Nature Biotechnology 15:866-870, describing the construction and use of adeno-retroviral chimeric vectors that can be employed for genetic modifications.

Additional references describing AAV vectors that could be used in the methods of the present invention include the following: Carter B. HANDBOOK OF PARVOVIRUSES, Vol. I, pp. 169-228, 1990; Berns, VIROLOGY, pp. 1743-1764 (Raven Press 1990); Carter B. (1992) Curr. Opin. Biotechnol. 3:533-539; Muzyczka N. (1992) Current Topics in Micro. and Immunol. 158:92-129; Flotte T. R. et al. (1992) Am. J. Respir. Cell Mol. Biol. 7:349-356; Chatterjee et al. (1995) Ann. NY Acad. Sci. 770:79-90; Flotte T. R. et al. WO 95/13365 (18 May 1995); Trempe J. P. et al., WO 95/13392 (18 May 1995); Kotin R. (1994) Hum. Gene Ther. 5:793-801; Flotte T. R. et al. (1995) Gene Therapy 2:357-362; Allen J. M. WO 96/17947 (13 Jun. 1996); and Du et al. (1996) Gene Therapy 3:254-261.

APCs can be transduced with viral vectors encoding a relevant polypeptide(s). The most common viral vectors include recombinant poxviruses such as vaccinia and fowlpox virus (Bronte et al. (1997) Proc. Natl. Acad. Sci. USA 94:3183-3188; Kim et al. (1997) J. Immunother. 20:276-286) and, preferentially, adenovirus (Arthur et al. (1997) J. Immunol. 159:1393-1403; Wan et al. (1997) Human Gene Therapy 8:1355-1363; Huang et al. (1995) J. Virol. 69:2257-2263). Retrovirus also may be used for transduction of human APCs (Marin et al. (1996) J. Virol. 70:2957-2962).

In vitro/ex vivo, exposure of human DCs to adenovirus (Ad) vector at a multiplicity of infection (MOI) of 500 for 16-24 h in a minimal volume of serum-free medium reliably gives rise to transgene expression in 90-100% of DCs. The efficiency of transduction of DCs or other APCs can be assessed by immunofluorescence using fluorescent antibodies specific for the tumor antigen being expressed (Kim et al. (1997) J. Immunother. 20:276-286). Alternatively, the antibodies can be conjugated to an enzyme (e.g., HRP) giving rise to a colored product upon reaction with the substrate. The actual amount of antigenic polypeptides being expressed by the APCs can be evaluated by ELISA.

Transduced APCs can subsequently be administered to the host via an intravenous, subcutaneous, intranasal, intramuscular or intraperitoneal route of delivery.

In vivo transduction of DCs, or other APCs, can be accomplished by administration of Ad (or other viral vectors) via different routes including intravenous, intramuscular, intranasal, intraperitoneal or cutaneous delivery. The preferred method is cutaneous delivery of Ad vector at multiple sites using a total dose of approximately $1 \times 10^{10}$-$1 \times 10^{12}$ i.u. Levels of in vivo transduction can be roughly assessed by co-staining with antibodies directed against APC marker(s) and the TAA being expressed. The staining procedure can be carried out on biopsy samples from the site of administration or on cells from draining lymph nodes or other organs where APCs (in particular DCs) may have migrated (Condon et al. (1996) Nature Med. 2:1122-1128 and Wan et al. (1997) Hum. Gene Ther. 8:1355-1363). The amount of antigen being expressed at the site of injection or in other organs where transduced APCs may have migrated can be evaluated by ELISA on tissue homogenates.

Although viral gene delivery is more efficient, DCs can also be transduced in vitro/ex vivo by non-viral gene delivery methods such as electroporation, calcium phosphate precipitation or cationic lipid/plasmid DNA complexes (Arthur et al. (1997) Cancer Gene Ther. 4:17-25). Transduced APCs can subsequently be administered to the host via an intravenous, subcutaneous, intranasal, intramuscular or intraperitoneal route of delivery.

In vivo transduction of DCs, or other APCs, can potentially be accomplished by administration of cationic lipid/plasmid DNA complexes delivered via the intravenous, intramuscular, intranasal, intraperitoneal or cutaneous route of administration. Gene gun delivery or injection of naked plasmid DNA into the skin also leads to transduction of DCs (Condon et al. (1996) Nature Med. 2:1122-1128; Raz et al (1994) Proc. Natl. Acad. Sci. USA 91:9519-9523). Intramuscular delivery of plasmid DNA may also be used for immunization (Rosato et al. (1997) Hum. Gene Ther. 8:1451-1458.)

The transduction efficiency and levels of transgene expression can be assessed as described above for viral vectors.

Adoptive Immunotherapy and Vaccines

The expanded populations of antigen-specific immune effector cells of the present invention also find use in adoptive immunotherapy regimes and as vaccines.

Adoptive immunotherapy methods involve, in one aspect, administering to a subject a substantially pure population of educated, antigen-specific immune effector cells made by culturing naïve immune effector cells with APCs as described above. Preferably, the APCs are dendritic cells.

In one embodiment, the adoptive immunotherapy methods described herein are autologous. In this case, the APCs are made using parental cells isolated from a single subject. The expanded population also employs T cells isolated from that subject. Finally, the expanded population of antigen-specific cells is administered to the same patient.

In a further embodiment, APCs or immune effector cells are administered with an effective amount of a stimulatory cytokine, such as IL-2 or a co-stimulatory molecule.

The agents identified herein as effective for their intended purpose can be administered to subjects having cell expressing CMV pp65 antigen as well as or in addition to individuals susceptible to or at risk. When the agent is administered to a subject such as a mouse, a rat or a human patient, the agent can be added to a pharmaceutically acceptable carrier and systemically or topically administered to the subject. To determine patients that can be beneficially treated, a tumor regression can be assayed. Therapeutic amounts can be empirically determined and will vary with the pathology being treated, the subject being treated and the efficacy and toxicity of the therapy.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

The agents and compositions of the present invention can be used in the manufacture of medicaments and for the treatment of humans and other animals by administration in accordance with conventional procedures, such as an active ingredient in pharmaceutical compositions.

More particularly, an agent of the present invention also referred to herein as the active ingredient, may be administered for therapy by any suitable route including nasal, topical (including transdermal, aerosol, buccal and sublingual), parental (including subcutaneous, intramuscular, intravenous and intradermal) and pulmonary. It will also be appreciated that the preferred route will vary with the condition and age of the recipient, and the disease being treated.

The preceding discussion and examples are intended merely to illustrate the art. As is apparent to one of skill in the art, various modifications can be made to the above without departing from the spirit and scope of this invention.

What is claimed is:

1. An isolated compound comprising the structure of SEQ ID NO:7.

2. A method for inducing an immune response in a subject, comprising delivering an effective amount of a compound of claim 1 to the subject.

\* \* \* \* \*

SEQUENCE LISTING

<160> NUMBER OF SEQ ID NOS: 15

<210> SEQ ID NO 1
<211> LENGTH: 1686
<212> TYPE: DNA
<213> ORGANISM: Homo sapiens

<400> SEQUENCE: 1

```
atggagtcgc gcggtcgccg ttgtcccgaa atgatatccg tactgggtcc catttcgggg      60
cacgtgctga aagccgtgtt tagtcgcggc gatacgccgg tgctgccgca cgagacgcga     120
ctcctgcaga cgggtatcca cgtacgcgtg agccagccct cgctgatctt ggtatcgcag     180
tacacgcccg actcgacgcc atgccaccgc ggcgacaatc agctgcaggt gcagcacacg     240
tactttacgg gcagcgaggt ggagaacgtg tcggtcaacg tgcacaaccc cacgggccga     300
agcatctgcc ccagccagga gcccatgtcg atctatgtgt acgcgctgcc gctcaagatg     360
ctgaacatcc ccagcatcaa cgtgcaccac tacccgtcgg cggccgagcg caaacaccga     420
cacctgcccg tagctgacgc tgtgattcac gcgtcgggca agcagatgtg gcaggcgcgt     480
ctcacggtct cgggactggc ctggacgcgt cagcagaacc agtggaaaga gcccgacgtc     540
tactacacgt cagcgttcgt gtttcccacc aaggacgtgg cactgcggca cgtggtgtgc     600
gcgcacgagc tggtttgctc catggagaac acgcgcgcaa ccaagatgca ggtgataggt     660
gaccagtacg tcaaggtgta cctggagtcc ttctgcgagg acgtgccctc cggcaagctc     720
tttatgcacg tcacgctggg ctctgacgtg gaagaggacc tgacgatgac ccgcaacccg     780 caaccccttca tgcgccccca cgagcgcaac ggctttacgg tgttgtgtcc caaaaatatg     840
ataatcaaac cgggcaagat ctcgcacatc atgctggatg tggcttttac ctcacacgag     900
cattttgggc tgctgtgtcc caagagcatc ccgggcctga gcatctcagg taacctgttg     960
atgaacgggc agcagatctt cctggaggta caagccatac gcgagaccgt ggaactgcgt    1020
cagtacgatc ccgtggctgc gctcttcttt ttcgatatcg acttgctgct gcagcgcggg    1080
cctcagtaca gcgagcaccc caccttcacc agccagtatc gcatccaggg caagcttgag    1140
taccgacaca cctgggaccg gcacgacgag ggtgccgccc agggcgacga cgacgtctgg    1200
accagcggat cggactccga cgaagaactc gtaaccaccg agcgcaagac gccccgcgtc    1260
accggcggcg gcgccatggc gggcgcctcc acttccgcgg gccgcaaacg caaatcagca    1320
```

-continued

```
tcctcggcga cggcgtgcac gtcgggcgtt atgacacgcg gccgccttaa ggccgagtcc    1380
accgtcgcgc ccgaagagga caccgacgag gattccgaca acgaaatcca caatccggcc    1440
gtgttcacct ggccgccctg gcaggccggc atcctggccc gcaacctggt gcccatggtg    1500
gctacggttc agggtcagaa tctgaagtac caggaattct tctgggacgc caacgacatc    1560
taccgcatct tcgccgaatt ggaaggcgta tggcagcccg ctgcgcaacc caaacgtcgc    1620
cgccaccggc aagacgcctt gcccgggcca tgcatcgcct cgacgcccaa aaagcaccga    1680
ggttga                                                                1686
```

<210> SEQ ID NO 2
<211> LENGTH: 561
<212> TYPE: PRT
<213> ORGANISM: Homo sapiens

<400> SEQUENCE: 2

```
Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
```

```
                    305                 310                 315                 320
Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser
            420                 425                 430

Ala Gly Arg Lys Arg Lys Ser Ala Ser Ser Ala Thr Ala Cys Thr Ser
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly

<210> SEQ ID NO 3
<211> LENGTH: 9
<212> TYPE: PRT
<213> ORGANISM: Homo sapiens

<400> SEQUENCE: 3

Phe Leu Leu Pro Met Ile Ala Thr Val
1               5

<210> SEQ ID NO 4
<211> LENGTH: 27
<212> TYPE: DNA
<213> ORGANISM: Homo sapiens
<220> FEATURE:
<221> NAME/KEY: misc_feature
<222> LOCATION: (6)..()
<223> OTHER INFORMATION: n = A,T,C, or G
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..()
<223> OTHER INFORMATION: n = A,T,C, or G
<220> FEATURE:
<221> NAME/KEY: misc_feature
<222> LOCATION: (9)..(9)
```

```
<223> OTHER INFORMATION: n is a, c, g, or t
<220> FEATURE:
<221> NAME/KEY: misc_feature
<222> LOCATION: (12)..()
<223> OTHER INFORMATION: n = A,T,C, or G
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..()
<223> OTHER INFORMATION: n = A,T,C, or G
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..()
<223> OTHER INFORMATION: n = A,T,C, or G
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..()
<223> OTHER INFORMATION: n = A,T,C, or G
<220> FEATURE:
<221> NAME/KEY: misc_feature
<222> LOCATION: (27)..(27)
<223> OTHER INFORMATION: n is a, c, g, or t

<400> SEQUENCE: 4
ttyytnytnc cnatgathgc nacngtn                                          27

<210> SEQ ID NO 5
<211> LENGTH: 9
<212> TYPE: PRT
<213> ORGANISM: Homo sapiens

<400> SEQUENCE: 5

Phe Leu Leu Trp Asp Trp Pro Phe Val
1               5

<210> SEQ ID NO 6
<211> LENGTH: 27
<212> TYPE: DNA
<213> ORGANISM: Homo sapiens
<220> FEATURE:
<221> NAME/KEY: misc_feature
<222> LOCATION: (6)..()
<223> OTHER INFORMATION: n = A, T, C or G
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..()
<223> OTHER INFORMATION: n = A, T, C or G
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (21)..()
<223> OTHER INFORMATION: n = A, T, C or G
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
```

-continued

```
<222> LOCATION: (27)..()
<223> OTHER INFORMATION: n = A, T, C or G
<220> FEATURE:
<221> NAME/KEY: misc_feature
<222> LOCATION: (27)..(27)
<223> OTHER INFORMATION: n is a, c, g, or t

<400> SEQUENCE: 6
ttyytnytnt gggaytggcc nttygtn                                          27

<210> SEQ ID NO 7
<211> LENGTH: 9
<212> TYPE: PRT
<213> ORGANISM: Homo sapiens

<400> SEQUENCE: 7

Phe Leu Phe Thr Arg Phe Met Arg Val
1               5

<210> SEQ ID NO 8
<211> LENGTH: 27
<212> TYPE: DNA
<213> ORGANISM: Homo sapiens
<220> FEATURE:
<221> NAME/KEY: misc_feature
<222> LOCATION: (6)..()
<223> OTHER INFORMATION: n = A, T, C, or G
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..()
<223> OTHER INFORMATION: n = A, T, C, or G
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..()
<223> OTHER INFORMATION: n = A, T, C, or G
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (24)..()
<223> OTHER INFORMATION: n = A, T, C, or G
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..()
<223> OTHER INFORMATION: n = A, T, C, or G
<220> FEATURE:
<221> NAME/KEY: misc_feature
<222> LOCATION: (27)..(27)
<223> OTHER INFORMATION: n is a, c, g, or t

<400> SEQUENCE: 8
ttyytnttya cnmgnttyat gmgngtn                                          27

<210> SEQ ID NO 9
<211> LENGTH: 9
<212> TYPE: PRT
<213> ORGANISM: Homo sapiens

<400> SEQUENCE: 9
```

```
Phe Leu Pro His Pro Gly Trp Leu Val
1               5

<210> SEQ ID NO 10
<211> LENGTH: 27
<212> TYPE: DNA
<213> ORGANISM: Homo sapiens
<220> FEATURE:
<221> NAME/KEY: misc_feature
<222> LOCATION: (6)..()
<223> OTHER INFORMATION: n = A, T, C, or G
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..()
<223> OTHER INFORMATION: n = A, T, C, or G
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..()
<223> OTHER INFORMATION: n = A, T, C, or G
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..()
<223> OTHER INFORMATION: n = A, T, C, or G
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..()
<223> OTHER INFORMATION: n = A, T, C, or G
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..()
<223> OTHER INFORMATION: n = A, T, C, or G
<220> FEATURE:
<221> NAME/KEY: misc_feature
<222> LOCATION: (27)..(27)
<223> OTHER INFORMATION: n is a, c, g, or t

<400> SEQUENCE: 10
ttyytnccnc ayccnggntg gytngtn                                        27

<210> SEQ ID NO 11
<211> LENGTH: 9
<212> TYPE: PRT
<213> ORGANISM: Homo sapiens

<400> SEQUENCE: 11

Phe Leu Ile Arg Leu Thr Pro Pro Val
1               5

<210> SEQ ID NO 12
<211> LENGTH: 27
<212> TYPE: DNA
<213> ORGANISM: Homo sapiens
<220> FEATURE:
<221> NAME/KEY: misc_feature
<222> LOCATION: (6)..()
```

```
<223> OTHER INFORMATION: n = A, T, C, or G
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..()
<223> OTHER INFORMATION: n = A, T, C, or G
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..()
<223> OTHER INFORMATION: n = A, T, C, or G
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..()
<223> OTHER INFORMATION: n = A, T, C, or G
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..()
<223> OTHER INFORMATION: n = A, T, C, or G
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..()
<223> OTHER INFORMATION: n = A, T, C, or G
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..()
<223> OTHER INFORMATION: n = A, T, C, or G
<220> FEATURE:
<221> NAME/KEY: misc_feature
<222> LOCATION: (27)..(27)
<223> OTHER INFORMATION: n is a, c, g, or t

<400> SEQUENCE: 12
ttyytnathm gnytnacncc nccngtn                                    27

<210> SEQ ID NO 13
<211> LENGTH: 9
<212> TYPE: PRT
<213> ORGANISM: Homo sapiens

<400> SEQUENCE: 13

Phe Leu Asp Phe Ser Phe Trp Phe Val
1               5

<210> SEQ ID NO 14
<211> LENGTH: 27
<212> TYPE: DNA
<213> ORGANISM: Homo sapiens
<220> FEATURE:
<221> NAME/KEY: misc_feature
<222> LOCATION: (6)..()
<223> OTHER INFORMATION: n = A, T, C, or G
<220> FEATURE:
<221> NAME/KEY: misc_feature
```

```
<222> LOCATION: (6)..(6)
<223> OTHER INFORMATION: n is a, c, g, or t
<220> FEATURE:
<221> NAME/KEY: misc_feature
<222> LOCATION: (15)..()
<223> OTHER INFORMATION: n = A, T, C, or G
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (27)..()
<223> OTHER INFORMATION: n = A, T, C, or G
<220> FEATURE:
<221> NAME/KEY: misc_feature
<222> LOCATION: (27)..(27)
<223> OTHER INFORMATION: n is a, c, g, or t

<400> SEQUENCE: 14
ttyytngayt tywsnttytg gttygtn                                           27

<210> SEQ ID NO 15
<211> LENGTH: 9
<212> TYPE: PRT
<213> ORGANISM: Homo sapiens

<400> SEQUENCE: 15

Asn Leu Val Pro Met Val Ala Thr Val
1               5
```